US007008771B1

(12) United States Patent
Schumm et al.

(10) Patent No.: US 7,008,771 B1
(45) Date of Patent: Mar. 7, 2006

(54) MULTIPLEX AMPLIFICATION OF SHORT TANDEM REPEAT LOCI

(75) Inventors: James W. Schumm, Madison, WI (US); Cynthia J. Sprecher, Madison, WI (US)

(73) Assignee: Promega Corporation, Madison, WI (US)

( * ) Notice: Subject to any disclaimer, the term of this patent is extended or adjusted under 35 U.S.C. 154(b) by 389 days.

(21) Appl. No.: 10/236,577

(22) Filed: Sep. 6, 2002

Related U.S. Application Data

(60) Division of application No. 09/199,542, filed on Nov. 25, 1998, now Pat. No. 6,479,235, which is a continuation-in-part of application No. 08/632,575, filed on Apr. 15, 1996, now Pat. No. 5,843,660, which is a continuation-in-part of application No. 08/316,544, filed on Sep. 30, 1994, now abandoned.

(51) Int. Cl.
C07H 21/04 (2006.01)
C12Q 1/68 (2006.01)

(52) U.S. Cl. .................. 435/6; 435/91.1; 435/91.2; 536/23.1; 536/24.3

(58) Field of Classification Search .............. 435/6, 435/91.1, 91.2; 536/23.1, 24.3
See application file for complete search history.

(56) References Cited

U.S. PATENT DOCUMENTS

| 4,683,195 A | 7/1987 | Mullis et al. |
| 4,683,202 A | 7/1987 | Mullis |
| 4,963,663 A | 10/1990 | White et al. |
| 5,175,082 A | 12/1992 | Jeffreys |
| 5,192,659 A | 3/1993 | Simons |
| 5,364,759 A | 11/1994 | Caskey et al. |
| 5,411,859 A | 5/1995 | White et al. |
| 5,422,252 A | 6/1995 | Walker et al. |
| 5,582,979 A | 12/1996 | Weber |
| 5,599,666 A | 2/1997 | Schumm et al. |
| 5,674,686 A | 10/1997 | Schumm et al. |
| 5,766,847 A | 6/1998 | Jäckle et al. |
| 5,783,406 A | 7/1998 | Schumm et al. |
| 5,843,660 A | 12/1998 | Schumm et al. |
| 6,479,235 B1 * | 11/2002 | Schumm et al. .............. 435/6 |

FOREIGN PATENT DOCUMENTS

| DE | 38 34 636 C2 | 4/1990 |
| WO | WO93/18177 | 9/1993 |
| WO | WO93/18178 | 9/1993 |
| WO | WO 96/10648 | 4/1996 |

OTHER PUBLICATIONS

Attachment #1, Sequence Alignments for SEQ ID No.: 1, 2, 7, 8, 11, 15, 16, 19, 20, 27, and 28.
Ballabio, A., et al., "Screening for Steroid Sulfatase (STS) Gene Deletions by Multiplex DNA Amplification," *Human Genetics* (1990) 84(6):571-573.
Caetano-Anolles, G., et al., "DNA Amplication Fingerprinting Using Arbitrary Oligonucleotide Primers," *Applied Biochemistry and Biotechnology* (1993) 42:189-200.
Fildes, N. J., et al., "AmpliType.RTM. PM Field Trial Results," *Program: Fourth International Symposium on Human Identification* (Sep. 27-29, 1993), p. 119.
Garofano, L. et al., (1998) Italian population data on thirteen short tandem repeat loci. *Forensic Science Int.* 97:53-60. PMID 9854840 [indexed for PubMed] Abstract.
Genbank Accession No: M18079, 1987.
Genbank Accession No: M21986, 1988.
Genbank Accession No: M22970, 1986.
Genbank Accession No: M25858, 1989.
Genbank Accession No: M26434, 1983.
Genbank Accession No: M28420, 1987.
Genbank Accession No: M64554, 1990.
Genbank Accession No: M68651, 1992.
Genbank Accession No: M87312, 1992.
Genbank Accession No: V00481, 1983.
Greenspoon, S. et al., (1998) QIAamp spin columns as a method of DNA isolation for forensic casework. *J. Foren. Sci.* 1024-1030.
Holgersson, S., et al., "Flourecent-Based Typing of the Two Short Tandem Repeat Loci HUMTH01 and HUMACTBP2: Reproducibility of Size Measurements and Genetic Variation in the Swedish Population" *Electrophoresis* (1994) 15:890-895.
Huber, P. and Holtz, J., "Random Priming and Multiplex PCR with Three Short Tandem Repeats for Forensic Casework," *Program: Fourth International Symposium on Human Identification* (Sep. 27-29, 1993) Scottsdale, AZ p. 220.
Huckenbeck, W., et al., "German Data on the HUJMVWA31 locus," *Anthrop. Anz.*, Jp. 54 1: 1-6 (Stuttgart, Mar. 1996) Abstract [PubMed PMID 8660000].
Kimpton, C., et al., "Automated DNA Profiling Employing Multiplex Amplification of Short Tandem Repeat Loci," *Adv. Forensic Haemogenet* (1994) 5:309-311.
Lorente, M., et al., "Sequential Multiplex Amplification of Genetic Markers from an Individual Sample," *Program: Fourth International Symposium on Human Identification* (Sep. 27-29, 1993) pp. 173-175.

(Continued)

*Primary Examiner*—Jeanine A. Goldberg
(74) *Attorney, Agent, or Firm*—Michael Best & Friedrich; Grady J. Frenchick

(57) ABSTRACT

Methods and materials are disclosed for use in simultaneously amplifying at least thirteen loci of genomic DNA in a single multiplex reaction, as are methods and materials for use in the analysis of the products of such reactions. Included in the present invention are materials and methods for the simultaneous amplification of at least thirteen short tandem repeat loci, including specific materials and methods for the analysis of thirteen such loci specifically selected by the United States Federal Bureau of Investigation as core loci for use in the Combined DNA Index System (CODIS) database.

6 Claims, 12 Drawing Sheets

OTHER PUBLICATIONS

Manam S., et al., "MultiPlex Polymerase Chain Reaction Amplification and Direct Sequencing of Homologous Sequences: Point Mutation Analysis of the ras Genes," *Anal. Biochem.* (1991) 199:106-111.

Micka K. et al., (1996) "Validation of Multiplex Polymorphic STR Amplification Sets Developed for Personal Identification Applications," *J. For. Sci.* Jul., 582-590.

Moretti, T., et al., (1998) "Enhancement of PCR Amplification Yield and Specificity Using AmpliTaq Gold DNA Polymerase," *Biotechniques.* 25:716-722.

Parkin, B., "The Development of Forensic DNA Profiling in the Metropolitan Police Forensic Science Laboratory," *Proceedings from the Third International Symposium on Human Identification* (1992) pp. 345-356.

Prior, T., et al., "A Model for Molecular Screening of Newborns: Simultaneous Detection of Duchenne/Becker Muscular Dystrophies and Cystic Fibrosis," *Clin. Chem.* (1990) 36(10):1756-1759.

Sajantila, A., et al., "Application of the Polymerase Chain Reaction in Forensic Medicine," *Proceedings from the Third International Symposium on Human Identification* (1992) pp. 375-381.

Salazar, M., "Genetic Typing of the DQA1*4 Alleles by Restriction Enzyme Digestion of the PCR Product Obtained with DQ Alpha Amplitype .TM. kit," *J. Forensic Sci.* (1993) 39:518-525.

Schmalzing, D. et al., (1999) "Two-color Multiplexed Analysis of Eight Short Tandem Repeat Loci with an Electrophoretic Microdevice," *Anal. Biochem.* 270:148-152.

Shuber, A. P., et al., "Efficient 12-Mutation Testing in the CFTR Gene: a General Model for Complex Mutation Analysis," *Hum. Mol. Genet.* (1993) 2(2):153-158.

Thomson, J., et al., (1999) "Validation of Short Tandem Repeat Analysis for the Investigation of Cases of Disputed Paternity," *Forensic Sci. Int.* 100:1-16. (Abstract—Downloaded from NCBI PubMed).

"Abstracts From The 42nd Annual C.S.F.S. Meeting," Toronto, Ontario, Sep. 26-30 (1995).

Alford, R. L., et al., "Rapid and Efficient Resolution of Parentage by Amplification of Short Tandem Repeats," *Am J. Hum Genet* (1994) 55: 190-195.

Anderson, Julia F. et al., "Further validation of a multiplex STR system for use in routine forensic identity testing," *Forensic Science International* (1996) 78: 47-64.

Anker, et al., "Tetranucleotide Repeat Polymorphism at the Human Thyroid Peroxidase (hTPA) Locus," (1992) vol. 1, No. 2.

Bassam, B.J., et al., "Fast and Sensitive Silver Straining of DNA in Polyacrylamide Gels," *Anal. Biochem..* (1991) 196:80-83.

Beckman, J.S. and Weber, J.L. "Survey of Human and Rat Microsatellites,".

Bever, Robert A., et al., "Validation and Utilization of Commercially Available STR Multiplexes for parentage Analysis," *Fifth International Symposium on Human Identification 1994* (1995): 61-68.

Budowie, Bruce, et al., "Validation and Population Studies of the Loci LDLR, GYPA, HBGG, D7S8, and Ge (PM loci), and HLA-DQα Using a Multiplex Amplification and Typing Procedure," (1995) 40(1): 45-54.

Chakraborty R. "A Class of Genetic Questions Formulated as the Generalized Occupancy Problem," *Genetics* (1993) 134: 953-958.

Chamberlain, J.S., et al., "Deletion screening of the Duchenne muscular dystrophy locus via multiplex DNA amplification," *Nucleic Acid Res.* (1988) 16: 11141-11156.

Chamberlain, J.S., et al. "Multiple PCR for the Diagnosis of Duchenne Muscular Dystrophy," (1989), *PCR Protocols, A Guide to Methods and Application,* pp. 272-281. (ed. Gelfand, D.H., et al.) Academic Press, San Diego, CA.

Clayton, T.M., et al., "Further validation of a quadruplex STR DNA typing system: a collaborative effort to identify victims of a mass disaster," *Forensic Science International* (1995) 76: 17-25.

Clemens, P.R., et al., "Carrier Detection and Prenatal Diagnosis in Duchenne and Becker Muscular Dystrophy Families, Using Dinucleotide Repeat Polymorphisms," *Am J. Human Genetics* (1991) 49: 951-960.

Covone, A.E., et al., "Screening Duchenne and Becker Muscular Dystrophy Patients for Deletions in 30 Exons of the Dystrophin Gene by Three-multiplex PCR," *Am J. Human Genetics* (1992) 51: 675-677.

Corach, Daniel, et al., "Mass disasters: Rapid molecular screening of human remains by means of short tandem repeats typing," *Electrophoresis* (1995) 16: 1617-1623.

Edwards, Al, et al., "DNA Typing with Trimeric and Tetrameric Tandem Repeats: Polymorphic Loci, Detection Systems, and Population Genetics," *Second International Symposium on Human Indentification* (1991), pp. 31-52.

Edwards, A. et al., "Genetic Variation at Five Trimeric and Tetrameric Tandem Repeat Loci in Four Human Population Groups," *Genomics* (1992) 12:241-253.

Edwards, M.C., and Gibbs, R.A. "Multiplex PCR: Advantages, Development, and Applications, " *PCR Methods and Applications* (1994) 3: S65-S75.

Eisenberg, Marcia, et al., "PCR for Identity Testing," *Fifth International Symposium on Human Identification 1994* (1995), pp. 103-107.

Estivill, X., et al., "Prenatal diagnosis of cystic fibrosis by multiplex PCR of mutation and microsatellite alleles," *Lancet* (1991) 338: 458.

Ferrie, R.M., et al., "Development, Multiplexing, and Applications of ARMS Tests for Common Mutations in the CTFR Gene," *Am J. Human Genetics* (1992) 51:251-262.

Fortina, P., et al., "Non-radioactive detection of the most common mutations in the cystic fibrosis transmembrane conductance regulator gene by multiplex polymerase chain reaction," *Human Genet.* (1992) 90: 3755-378.

Fregeau, C.J., et al., "PCR-Based DNA Identification A Transition in Forensic Science," *Fourth International Symposium on Human Identification* (1993), pp. 107-117.

Furedit, Sandor, et al., "Hungarian Population Data on Six STR Loci-HUMVWFA31, HUMTH01, HUMCSF1PO, HUMFES?FPS, HUMTPOX, and HUMHPRTB-derived using multiplex PCR amplification and manual typing," *Springer-Verlag* (1996), pp. 100-101.

Gibbs, R.A., et al., "Multiple DNA Deletion Detection and Exon Sequencing of the Hypoxanthine Phosphoribosyltransferase Gene in Lesch-Nyhan Families," *Genomics* (1990) 7: 235-244.

Gill, P. et al., "Forensic Application of DNA 'Fingerprints'," *Nature* (1985) 318: 577-579.

Gyapay, Gabor, et al., "Genotyping Procedures in Linkage Mapping," *Academic Press, Inc.* (1996) 9: 91-97.

Hammond, Holly, et al., "Personal Identification via Short Tandem Repeats," *Third International Symposium on Human Identification* (1992), pp. 163-175.

Hausmann, R. et al., "Frequencies of the 5 PCR-based genetic markers LDLR, GYPA, HBGG, D7S8, and GC in a North Bavarian population," *Springer-Verlag* (1995), pp. 227-228.

Hochmeister, M.N., et al., "Swiss Caucasian Population Data and Casework-Applications Using PCR Amplification Kits," *Fifth International Symposium on Human Identification 1994* (1995), pp. 51-60.

Hochmeister, et al., "Swiss Population Data on Three Tetrameric Short Tandem Repeat Loci VWA, HUMTH01, and F13A1 Derived using Multiplex PCR and Laser Fluorescence Detection," *International Journal of Legal Medicine*, (1994) 107(1):34-36.

Hochmeister, et al., "A Method for the Purification and Recovery of Genomic DNA from an HLA DQA1 Amplification Product and Its Subsequent Amplification and Typing with the AmpliType® PM PCR Amplification and Typing Kit," *Journal of Forensic Sciences, JFSCA* (1995) 40(4): 649-653.

Hochmeister, et al., "Using Multiplex PCR Amplification and Typing Kits for the Analysis of DNA Evidence in a Serial Killer Case," *Journal of Forensic Sciences, JFSCA* (1996) 41(1): 155-162.

Hochmeister, et al., Confirmation of the Identity of Human Skeletal Remains Using Multiplex PCR Amplification and Typing Kits, *Journal of Forensic Sciences, JFSCA* (1995) 40(4): 701-705.

Huang, Nu En, et al., "Chinese popluation data on three tetrameric short tandem repeat loci-HUMTH01, TPOX, and CSF1PIO-derived using multiplex PCR and manual typing," *Forensic Science International* (1995) 71: 131-136.

Huang, T.H.-M., et al., "Genetic Mapping of Four Dinucleotide Repeat Loci DXS435, DXS45, DXS454, DXS424, on the X Chromosome Using the Multiplex Polymerase Chain Reaction," *Genomics* (1992) 13:375-380.

Hudson, Thomas, et al., "Isolation and Chromosmal Assignment of 100 Highly Informative Human Simple Sequence Repeat Polymorphisms," *Genomics* (1992) 13:622-629.

Kimpton, C., et al., "Evaluation of an automated DNA progiling system employing multiplex amplification of four tetrameric STR loci," *Int, J. Leg. Med.* 106: 302-311 (spring 1994).

Kimpton, Colin, et al., "Automated DNA Profiling Employing Multiplex Amplification of Short Tandem Repeat Loci," *PCR Methods and Applications* (1993), pp. 13-22.

Laird, John, et al., "Ontario Caucasian Population Data at Four Short Tandem Repeat (STR) Loci (vWa, TH01, F13A1, FES/FPS) Ampified as a Multiplex and Analyzed by Automated Fluorescence Detection," *Fifth International Symposium on Human Identification 1994* (1995), pp. 169-170.

Lohmann, D., et al., "Detection of Small RB1 gene deletions in retinolastoma by multiplex PCR and high-resolution gel electrophoresis," *Hum. Genet.* (1992) 89: 49-53.

Lee, Steven B. et al., "Microwave Extraction, Rapid DNA Quantitation and Fluorescent Detection of Amplified Short Tandem Repeats," *Fifth International Symposium on Human Identification 1994* (1995), pp. 137-145.

Lygo, et al., "The Validation of Short Tandem Repeat (STR) Loci for use in Forensic Casework," *International Journal of Legal Medicine*, (1994) 107(2): 77-89.

Morral, N. and Estivill, X. "Multiplex PCR Amplification of Three Microsatellites within the CFTR Gene," *Genomics* (1992) 51: 1362-1364.

Patel PI, et al., "Organization of the JPRT Gene and Related Sequences in the Human Genome," *Somat Cell Mol. Genet* (1984) 10: 483-493.

Pftizinger, Helene, et al., "French experience in STR Systemns: Caucasian Population DataBases, Automated Fluorescent Quadruplex Typing and Forensic Applications for HUMFESFPS, HUMTH01, HUMVWA31/A and HUMF13A1 Loci," *Fifth International Symposium on Human Identification 1994* (1995), pp. 85-94.

Promega, "GenePrint Fluorescent STR Systems," *Technical Manual TMD006*, Dec. 1994.

Promega, "GenePrint STR Systems," *Technical Manual TMD004*, Oct. 1994.

Rosen, B., et al., "Rapid DNA Profiling Using Microsatellites, PCR and Fluorescent DNA Typing," *Fourth International Symposium on Human Identification* (1993), pp. 228-229.

Ricciardone, Marie, et al., "Evaluation of Fluorescent GenePrint™ Multiplex STR Systems on the 373 DNA Sequencer," *Fifth International Symposium on Human Identification 1994* (1995), pp. 173.

Richard, Malanie, et al., "Validation Studies of Four Short Tandem Repeat (STR) Repeat (STR) Loci (vWA, THO01, F13A1, and FES/FPS) Amplified as a Multiplex and Analyzed by Automated Flyorescence Detection," *Fight International Symposium on Human Identification 1994* (1995), pp. 174.

Schumm, James W., et al., "Validation of Multiplex Polymorphic STR Amplification Sets Developed for Personal Identification Applications," *Fifth International Symposium on Human Identification 1994* (1995), pp. 49.

Schumm, James W., et al., "Analysis of Short Tandem Repeats: High Throughput Nonisotopic Methods for Every Laboratory," *Practical Techniques in DNA Analysis of PCR Fragments* pp. 41-62 (Handout at a Workshop help in Scottsdale Sep. 26, 1993).

Schumm, James W., et al., "Development of Nonisotopic Multiplex Amplification Sets for Analysis of Polymorphic STR Loci," *Fourth International Symposium on Human Indentification* (1993), pp. 177-187.

Schwartz, J.S., et al., "Fluorescent Multiple Linkage Analysis and Carrier Detection for Duchenne/Becker' Muscular Dystrophy," *Am J. Hum. Genet.* (1992) 51: 721-729.

Shuber, Anthony, "A Simplified Procedure for Developing Multiplex PCPs" *Genome Research by Cold Spring Harbor Laboratory Press ISSN* (1995) 5: 488-493.

Sjerps, Marjan et al., "A Dutch Population Study of the STR loci HUMTH01, HUMFES/FPS, HUMVWA31/1 and HUMF13A1, conducted on forensic purposes," *Springer-Verlag* (1996), pp. 127-134.

Sparkes, R. et al., "The Validation of a 7-locus multiplex STR test for use in forensic casework I and II,"*Springer-Verlag* (1996) 109: 186-194.

Tautz, D., et al., "Cryptic simplicity in DNA is a major source of genetic variation," *Nature* (1986) 322:652-656.

Urquhart, A., et al., "Variation in Short Tandem Repeat sequences-a survey of twelve microsatellite loci for use as forensic identification markers," *Int. J. Leg. Med* (1994) 107: 13-20.

Urquhart, A., et al., "Highly Discriminating Heptalpex Short Tandem Repeat PCR System for Forensic Identification," *BioTechniques* (1995) 18(1): 117-121.

Urquhart, A., et al., "Multiplex STR Systems with Fluorescent Detection as Human Identification Markers,"

*Fifth International on Human Identification 1994* (1995), pp. 73-94.

Weber, J.L. and May, P.E. "Abundant Class of Human DNA Polymorphisms Which can be Typed Using the Polymerase Chain Reaction," *Am. J Hum. Genet.* (1989) 44:388-396.

Williamson, R, et al., "Report of the DNA committee and cataloques of cloned and mapped genes and DNA polymorphisms," *Cytogenet Cell Cenet* (1990) 55: 457-778.

Worley, Jennifer M., et al., "Rapid Genetic Typing on the FluorImager: Human DNA Quantitation, RFLP, DIS80, and Short Tandem Repeat (STR) Analysis," *Fifth International Symposium on Human Identification 1994* (1995), pp. 109-116 and pp. 154-158.

Miller, S. A. et al., "A simple salting out procedure for extracting DNA from human nucleated cells", (1988) *Nucleic Acids Research*, vol. 16, No. 3: 1215.

Walsh, P. S. et al., "Chelex® 100 as a Medium for Simple Extraction of DNA for PCR-Based Typing from Forensic Material," *Biotechniques*, vol. 10, No. 4, pp. 506-513.

Burckhardt, J., (1994) "Amplification of DNA from Whole Blood," *PCR Methods and Applications*, pp. 239-243.

McCabe, E. R. (1991) "Utility of PCR for DNA Analysis from Dried Blood Sports on Filter Paper Blotters," *PCR Methods and Applications*, 1:99-106.

Nordväg, B.Y., et al. (1992) "Direct PCR of Washed Blood Cells," *BioTechniques* vol. 12 No. 4, pp. 490-492.

Schumm, J. W., et al., (1998) "A Validated Nine-Locus Multiplex System for STR Allele Determinations," in "The Proceedings of the American Academy of Forensic Sciences," B88, pp. 53.

Gibson, S.D., et al., (1998) "Validation of the PowerPlex™ STR System and DQA1, PM and PowerPlex™ Genotype Frequencies in the Palm Beach Databases," in "The Proceedings of the American Academy of Forensic Sciences," B89, pp. 53.

Lazaruk, K., et al., (1998) "TWGDAM and Beyond: Performance of AmpFISTR Multiplexes on Difficult Samples," in "The Proceedings of the American Academy of Forensic Sciences," B83, pp. 51.

Sparkes, R., et al. (1996) "The validation of a 7-locus multiplex STR test for use in forensic casework," *Int. J. Legal Med.* 109: 186-194.

Perkin-Elmer Corporation, (1997) *AmpFISTR Profiler™ PCR Amplification Kit User's Manual*, pp. 1-1-1.10.

Perkin-Elmer Corporation, (1997) *AmpFISTR Profiler Plus™ PCR Amplification Kit User's Manual*, pp. 1-1-1.10.

Perkin-Elmer Corporation, (1997) *AmpFISTR CoFiler™ PCR Amplification Kit User Bulletin pp.* pp. 1-1-1.10.

Staub, R. W., et al., (1998) "Real Time Paternity Testing Utilizing a Novel 11-System STR Multiplex Analyzed on an ABI Prism 377 DNA Sequencer," in "Poster Abstracts from the Ninth International Symposium on Human Identification," p. 8.

Willard, J. M., et al., (1998) "Mixed Sample Evaluation Using AmpFISTR Profiler Plus™ on the ABI Prism 310 Genetic Analyzer and ABI 377 DNA Sequencer," in "Poster Abstracts from the Ninth International Symposium on Human Identification," p. 73.

Walsh, P. S., et al., (1998) "Continuous Evolution of DNA Typing Systems for Forensic Casework and High Throughput Databanks," in "Speaker Abstracts from the Ninth International Symposium on Human Identification," 1 pg.

Schumm, J. W., et al. (1997) "Automated Fluorescent Detection of 8-locus and 4-locus STR Multiplexes," in "Proceedings from the Eighth Interneational Symposium on Human Identication," pp. 78-84.

Buel, E., et al., (1998) "Capillary Electrophoresis STR Analysis: Comparsion to Gel-Based Systems." *J. Forensic Sci.* 43(1): 164-170.

Niezgoda, S. J., (1997) "Taking CODIS Nationwide: Status and Program Update," *Cambridge Healthtech Institute's Second Annual Conference on DNA Forensics*, pp. 1-21.

Niezgoda, S. J., (1997) "CODIS Program Overview," in "Proceedings from the Eighth International Symposium on Human Identification," pp. 48-49.

Niezgoda, S. J., (1997) "CODIS Program Overview," *Profiles in DNA*, vol. 1, No. 3, pp. 12-13.

Frazier, R. R. E., et al., (1997) "STR Profiling Methods and the UK National Criminal Intelligence DNA Database," in "Proceedings from the Eighth International Symposium on Human Identification," pp. 56-60.

Werrett, D. J., et al, (1998) "300 Matches per Week—The Effectiveness and Future Development of DNA Intelligence Databases," in "Speaker Abstracts from the Ninth Inteternational Symposium on Human Identification," pp. 5-6.

Budowie, B. et al., (1998) "CODIS Genetic Marker Databases," in "Speaker Abstracts from the Ninth International Symposium on Human Identification," 1 pg.

Puers, C., (1994) "Allelic Ladder Characterization of the Short Tandem Repeat Polymorphism Located in the 5' Flanking Region to the Human Coagulation Factor XIII A Subunit Gene," *Genomics.*, 32:260-264.

Weber, J. L., et al., (1989) "Abundant Class of Human DNA Polymorphism Which Can Be Typed Using the Polymerase Chain Reaction," *Am. J. Hum. Gent.* 44: 388-396.

Nakamura, Y., et al., "Variable Number of Tandem Repeat (VNTR) Markers for Human Gene Mapping." (1987) *Science* 235: 1616-1622.

Jeffreys, A. J., et al. "Hypervariable 'minisatellite' regions in human DNA," (1985) *Nature* 314:67-73.

Edwards et al. "DNA Typing and Genetic Mapping with Trimeric and Terameric Tandem Repeats," (1991) *Am. J. Hum. Genet.* 49:746-756.

Frégeau, C. J., et al. "DNA Typing with Fluorescently Tagged Short Tandem Repeats: A Sensitive and Accurate Approach to Human Identification," (1993) *BioTechniques*, vol 15, No. 1, pp. 100-119.

Schumm, J. W., et al., "Development of Nonisotopic Multiplex Amplification Sets for Analysis of Polymorphic STR Loci," (1993) *Fourth International Symposium on Human Indentication*, pp. 177-187.

Presley, L. A., et al. (1993) "The Implementation of the Polymerase Chain Reaction (PCR) HLA DQ Alpha Typing by the FBI Laboratory," in "The Third International Symposium on Human Identification 1992," pp. 245-269.

Bever, R. A., et al. (1992) "Characterization of Five VNTR Loci by *Hae* III RFLP Analysis: Application to Paternity Testing," in "The Second International Symposium on Human Identification 1991," pp. 103-128.

Waye, J. S., et al. (1991) "Sensitive and Specific Quantification of Human Genomic Deoxyribonucleic Acid (DNA) in Forensic Science Specimens: Casework Examples," *J. Forensic Sci.*, vol. 36, No. 4, pp. 1198-1203.

Saiki, R. K., et al. (1985) "Enzymatic Amplification of βGlobin Genomic Sequences and Restriction Site Analysis for Diagnosis of Sickle Cell Anemia," *Science* 230: 1350-1354.

Kwoh, D. Y., et al. (1990) "Target amplification systems in nucleic acid-based diagnostic approaches," *American Biotechnology Laboratory*, Oct., 1990, pp. 14-25.

Walker, G. T., et al. (1992) "Isothermal in vitro amplification of DNA by a restrication enzyme/DNA polymerase system," *Proc. Natl. Acad. Sci., U.S.A.* 89: 392-396.

Sambrook, J., et al. (1989) In *Molecular CloningCA Laboratory Manual*, 2nd edition, Cold Spring Harbor Laboratory Press, pp. 13.45-13.57.

Puers, C., et al. (1993) "Identification of Repeat Sequence Heterogeneity at the Polymorphic Short Tandem Repeat Locus HUMTH01[AATG], and Reassignment of Alleles in Population Analysis by Using a Locus-specific Allelic Ladder." *Am. J. Hum. Genet.* 53: 953-958.

Kobayashi, Y. (1988) "A Method to Cast Thin Sequencing Gels," *BRL Focus* 10: 73-74.

Brunk C. F., et al. 4 (1979) "Assay for Nanogram Quantities of DNA in Cellular Homogenates," *Analytical Biochemistry* 92: 497-500.

Sambrook, J., et al. (1989) *Molecular Cloning A Laboratory Manual*, Second Edition, Cold Spring Harbor Laboratory Press, Appendix E-5.

Southern, E. M., "Detection of Specific Sequences Among DNA Frangments Separated by Gel Electrophoresis," (1975) *J. Mol. Biol.* 98, pp. 503-517.

Schumm, J. W., et al., "Identication of More than 500 RFLP's by Screening Random Genomic Clones," (1988) *Am. J. Hum. Genet.* 42:143-159.

Wyman, A. R., et al., "A highly polymorphic locus in human DNA," (1980) *Proc. Natl. Acad. Sci. USA*, vol. 77, No. 11 pp. 6754-6758.

Jeffreys, A. J., et al., "Individual-specific 'fingerprints' of human DNA," (1985) *Nature*, vol. 316, pp. 76-79.

Decorte, R., et al., "Rapid Detection of Hypervariable Regions by the Polymerase Chain Reaction Technique," (1990) *DNA and Cell Biology*, vol. 9, No. 6, pp. 461-469.

Kasai, K., et al., "Amplification of a Variable Number of Tandem Repeats (VNTR) Locus (pMCT118) by the Polymerase Chain Reaction (PCR) and Its Application to Forensic Science," (1990) *Journal of Forensic Sciences*, JFSCA, vol. 35, No. 5, pp. 1196-1200.

Tautz, D., "Hypervariablilty of simple sequences as a general source for polymorphic DNA markers," (1989) *Nucleic Acids Research*, vol. 17, No. 16, pp. 6463-6471.

Edwards, M. C., et al., "Pentanucleotide repeat length polymorphism at the human CD4 locus,"(1991) *Nucleic Acids Research*, vol. 19, No. 17 p. 4791.

Chen, H., et al., "A Novel Zinc Finger cDNA with a Polymorphic Pentanucleotide Repeat (ATTTT), Maps on Human Chromosome 19p," (1993) *Genomics* 15, pp. 621-625.

Comings, D. E., et al., "Sequence of Human Tryptophan 2,3-Dioxygenase (TDO2): Presence of a Glucocirticoid Response-like Element Composed of a GTT Repeat and an Intronic CCCCT Repeat," (1995), *Genomics* 29, pp. 390-396.

Jurka, J., et al., "Simple Repetitive DNA Sequences from Primates: Compilation and Analysis," (1995) *J. Mol. Evol.*, 40:120-126.

Ponce, M. R., et al., "PCR amplification of long DNA fragments," (1992) *Nucleic Acids Research* vol. 20, No. 3, p. 623.

Litt, M., et al. "A Hypervariable Microsatellite Revealed by In Virto Amplification of a Dinucleotide Repeat within the Cardiac Muscle Actin Gene," (1989) *Am. J. Hum. Genet.* 44: 397-401.

Adamson, D., et al. "A Collection of Ordered Tetranucleotide-Repeat Markers from the Human Genome," (1995) *Am. J. Hum. Genet.* 57:619-628.

Hammond, H. A., et al. "Evaluation of 13 Short Tandem Repeat Loci for Use in Personal Identification Applications," (1994) *Am. J. Hum. Genet.* 55: 175-189.

Promega, (1997) *GenePrint™ PowerPlex™ 1.1 System Technical Manual*, pp. 1-36.

Promega, (1998) *GenePrint™ PowerPlex™ 1.2 System Technical Manual*, pp. 1-36.

Promega, (1998) *GenePrint™ PowerPlex™ 2.2 System Protoype Technical Manual*, pp. 1-35.

Promega, (1998) *GenePrint™ STR Systems (Silver Stain Detection) Technical Manual* pp. 1-52.

Schumm, J. W, "Construction and Use of Allelic Ladders for the STR Systems HUMTH01, HUMCSF1P0, and HUMFESFPS" Apr. 1, 1993, The Second International Symposium on the Forensic Aspects of DNA Analysis (schedule of speakers), 4 pgs.

Schumm, J. W., et al., "Analysis of Short Tandem Repeats", Practical Techniques in DNA Analysis of PCT Fragments, Sep. 26, 1993, pp. 41-62.

Sambrook, J., et al. (1989) *Molecular Cloning: A Laboratory Manual. Second Edition*, Cold. Spring Harbor Laboratory Press, Cold Spring Harbor, New York., pp. 9-14-9.19.

Comey, C., et al. (1994) "DNA Extraction Strategies for Amplified Fragment Length Polymorphism Analysis." *J. Forensic Sci.* 39: 1254-1269.

Armour, J., et al., "Isolation of human simple repeat loci by hybridization selection," (1994) *Human Molecular Genetics*, vol. 3, No. 4, pp. 599-605.

Niezgoda, Stephen J. Jr., et al. "The FBI Laboratory's Combined DNA Index System Program", (1995) *The Sixth International Symposium on Human Identification*, pp. 149-153.

* cited by examiner

Amplification with DNA template

Amplification with NO DNA template

Amplification with DNA template

Amplification with NO DNA template

Amplification with DNA template

Amplification with NO DNA template

505nm Scan: Fluorescein Channel

FIG 4B

585nm Scan: Tetramethyl Rhodamine Channel

Sample 1    Sample 2
1  2  3     1  2  3

HUMFIBRA

HUMTPOX

D8S1179

HUMvWFA31

Amelogenin

505nm Scan: Fluorescein Channel

FIG 5B

585nm Scan: Tetramethyl Rhodamine Channel

```
              Sample 1    Sample 2
               1   2       1   2
```

HUMFIBRA

HUMTPOX

D8S1179

HUMvWFA31

Amelogenin

505nm Scan: Fluorescein Channel

585nm Scan: Tetramethyl Rhodamine Channel

SEQUENCE LISTING

```
<160> NUMBER OF SEQ ID NOS: 110

<210> SEQ ID NO 1
<211> LENGTH: 24
<212> TYPE: DNA
<213> ORGANISM: Homo sapien
<222> LOCATION: D7S820

<400> SEQUENCE: 1
gaacacttgt catagtttag aacg                                        24

<210> SEQ ID NO 2
<211> LENGTH: 23
<212> TYPE: DNA
<213> ORGANISM: Homo sapien
<222> LOCATION: D7S820

<400> SEQUENCE: 2
ctgaggtatc aaaaactcag agg                                         23
```

<210> SEQ ID NO 3
<211> LENGTH: 20
<212> TYPE: DNA
<213> ORGANISM: Homo sapien
<222> LOCATION: D13S317

<400> SEQUENCE: 3
acagaagtct gggatgtgga					20

<210> SEQ ID NO 4
<211> LENGTH: 20
<212> TYPE: DNA
<213> ORGANISM: Homo sapien
<222> LOCATION: D13S317

<400> SEQUENCE: 4
gcccaaaaag acagacagaa					20

<210> SEQ ID NO 5
<211> LENGTH: 20
<212> TYPE: DNA
<213> ORGANISM: Homo sapien
<222> LOCATION: D5S818

<400> SEQUENCE: 5
gggtgatttt cctctttggt					20

<210> SEQ ID NO 6
<211> LENGTH: 20
<212> TYPE: DNA
<213> ORGANISM: Homo sapien
<222> LOCATION: D5S818

<400> SEQUENCE: 6
tgattccaat catagccaca					20

<210> SEQ ID NO 7
<211> LENGTH: 26
<212> TYPE: DNA
<213> ORGANISM: Homo sapien
<222> LOCATION: D3S1539

<400> SEQUENCE: 7
tctctttcca ttactctctc catagc				26

<210> SEQ ID NO 8
<211> LENGTH: 22
<212> TYPE: DNA
<213> ORGANISM: Homo sapien
<222> LOCATION: D3S1539

<400> SEQUENCE: 8
agtgctgttt tagcttccag ga				22

<210> SEQ ID NO 9
<211> LENGTH: 24
<212> TYPE: DNA
<213> ORGANISM: Homo sapien
<222> LOCATION: D17S1298

<400> SEQUENCE: 9
gtaggtcttt tggttgccag tatg				24

<210> SEQ ID NO 10
<211> LENGTH: 24
<212> TYPE: DNA
<213> ORGANISM: Homo sapien
<222> LOCATION: D17S1298

<400> SEQUENCE: 10
tgtcagtaaa cctgtgacct gagt                                    24

<210> SEQ ID NO 11
<211> LENGTH: 26
<212> TYPE: DNA
<213> ORGANISM: Homo sapien
<222> LOCATION: D20S481

<400> SEQUENCE: 11
aatggtgaga aatgggttat gagtgc                                  26

<210> SEQ ID NO 12
<211> LENGTH: 25
<212> TYPE: DNA
<213> ORGANISM: Homo sapien
<222> LOCATION: D20S481

<400> SEQUENCE: 12
tttccggctt tgtgtcataa aacag                                   25

<210> SEQ ID NO 13
<211> LENGTH: 20
<212> TYPE: DNA
<213> ORGANISM: Homo sapien
<222> LOCATION: D9S930

<400> SEQUENCE: 13
tggacaacag agtgagatgc                                         20

<210> SEQ ID NO 14
<211> LENGTH: 23
<212> TYPE: DNA
<213> ORGANISM: Homo sapien
<222> LOCATION: D9S930

<400> SEQUENCE: 14
gctatgggaa ttacaagcag gaa                                     23

<210> SEQ ID NO 15
<211> LENGTH: 26
<212> TYPE: DNA
<213> ORGANISM: Homo sapien
<222> LOCATION: D10S1239

<400> SEQUENCE: 15
ctttgaaatg gacccctagc taatgt                                  26

<210> SEQ ID NO 16
<211> LENGTH: 21
<212> TYPE: DNA
<213> ORGANISM: Homo sapien
<222> LOCATION: D10S1239

<400> SEQUENCE: 16
caccctgtcc ccagctatct g                                       21

<210> SEQ ID NO 17
<211> LENGTH: 19

```
<212> TYPE: DNA
<213> ORGANISM: Homo sapien
<222> LOCATION: D14S118

<400> SEQUENCE: 17
cagcttgggc aacataggg                                                    19

<210> SEQ ID NO 18
<211> LENGTH: 24
<212> TYPE: DNA
<213> ORGANISM: Homo sapien
<222> LOCATION: D14S118

<400> SEQUENCE: 18
caaactcctg aggtcaaaca atcc                                              24

<210> SEQ ID NO 19
<211> LENGTH: 21
<212> TYPE: DNA
<213> ORGANISM: Homo sapien
<222> LOCATION: D14S562

<400> SEQUENCE: 19
cttggagggt ggggtggcta a                                                 21

<210> SEQ ID NO 20
<211> LENGTH: 24
<212> TYPE: DNA
<213> ORGANISM: Homo sapien
<222> LOCATION: D14S562

<400> SEQUENCE: 20
cgaaattttg ttgccttgct ctgg                                              24

<210> SEQ ID NO 21
<211> LENGTH: 21
<212> TYPE: DNA
<213> ORGANISM: Homo sapien
<222> LOCATION: D14S548

<400> SEQUENCE: 21
cctgggcaac agagtgagac t                                                 21

<210> SEQ ID NO 22
<211> LENGTH: 24
<212> TYPE: DNA
<213> ORGANISM: Homo sapien
<222> LOCATION: D14S548

<400> SEQUENCE: 22
acccagcttt aacagtttgt gctt                                              24

<210> SEQ ID NO 23
<211> LENGTH: 23
<212> TYPE: DNA
<213> ORGANISM: Homo sapien
<222> LOCATION: D16S490

<400> SEQUENCE: 23
gggcggacac agaatgtaaa atc                                               23

<210> SEQ ID NO 24
<211> LENGTH: 24
<212> TYPE: DNA
<213> ORGANISM: Homo sapien
```

-continued

```
<222> LOCATION: D16S490

<400> SEQUENCE: 24 aacccaaat agatgacagg caca                                              24

<210> SEQ ID NO 25
<211> LENGTH: 24
<212> TYPE: DNA
<213> ORGANISM: Homo sapien
<222> LOCATION: D16S753

<400> SEQUENCE: 25
gcactccagg ctgaatgaca gaac                                             24

<210> SEQ ID NO 26
<211> LENGTH: 24
<212> TYPE: DNA
<213> ORGANISM: Homo sapien
<222> LOCATION: D16S753

<400> SEQUENCE: 26
gcagtgccgc ctattttgt gaat                                              24

<210> SEQ ID NO 27
<211> LENGTH: 24
<212> TYPE: DNA
<213> ORGANISM: Homo sapien
<222> LOCATION: D17S1299

<400> SEQUENCE: 27
accctgatga gatagcactt gagc                                             24

<210> SEQ ID NO 28
<211> LENGTH: 24
<212> TYPE: DNA
<213> ORGANISM: Homo sapien
<222> LOCATION: D17S1299

<400> SEQUENCE: 28
cactgtgtgg aggtgtagca gaga                                             24

<210> SEQ ID NO 29
<211> LENGTH: 24
<212> TYPE: DNA
<213> ORGANISM: Homo sapien
<222> LOCATION: D16S539

<400> SEQUENCE: 29
gggggtctaa gagcttgtaa aaag                                             24

<210> SEQ ID NO 30
<211> LENGTH: 26
<212> TYPE: DNA
<213> ORGANISM: Homo sapien
<222> LOCATION: D16S539

<400> SEQUENCE: 30
tgtgcatctg taagcatgta tctatc                                           26

<210> SEQ ID NO 31
<211> LENGTH: 23
<212> TYPE: DNA
<213> ORGANISM: Homo sapien
<222> LOCATION: D22S683
```

-continued

<400> SEQUENCE: 31
cgaaggttgc attgagccaa gat                          23

<210> SEQ ID NO 32
<211> LENGTH: 23
<212> TYPE: DNA
<213> ORGANISM: Homo sapien
<222> LOCATION: D22S683

<400> SEQUENCE: 32
ggtggaaatg cctcatgtag aaa                          23

<210> SEQ ID NO 33
<211> LENGTH: 24
<212> TYPE: DNA
<213> ORGANISM: Homo sapien
<222> LOCATION: HUMCSF1PO

<400> SEQUENCE: 33
aacctgagtc tgccaaggac tagc                         24

<210> SEQ ID NO 34
<211> LENGTH: 24
<212> TYPE: DNA
<213> ORGANISM: Homo sapien
<222> LOCATION: HUMCSF1PO

<400> SEQUENCE: 34
ttccacacac cactggccat cttc                         24

<210> SEQ ID NO 35
<211> LENGTH: 24
<212> TYPE: DNA
<213> ORGANISM: Homo sapien
<222> LOCATION: HUMTPOX

<400> SEQUENCE: 35
actggcacag aacaggcact tagg                         24

<210> SEQ ID NO 36
<211> LENGTH: 24
<212> TYPE: DNA
<213> ORGANISM: Homo sapien
<222> LOCATION: HUMTPOX

<400> SEQUENCE: 36
ggaggaactg ggaaccacac aggt                         24

<210> SEQ ID NO 37
<211> LENGTH: 24
<212> TYPE: DNA
<213> ORGANISM: Homo sapien
<222> LOCATION: HUMTHO1

<400> SEQUENCE: 37
attcaaaggg tatctgggct ctgg                         24

<210> SEQ ID NO 38
<211> LENGTH: 24
<212> TYPE: DNA
<213> ORGANISM: Homo sapien
<222> LOCATION: HUMTHO1

<400> SEQUENCE: 38

-continued gtgggctgaa aagctcccga ttat　　　　　　　　　　　　　　　　24

<210> SEQ ID NO 39
<211> LENGTH: 29
<212> TYPE: DNA
<213> ORGANISM: Homo sapien
<222> LOCATION: HUMvWFA31

<400> SEQUENCE: 39
gaaagcccta gtggatgata agaataatc　　　　　　　　　　　　　29

<210> SEQ ID NO 40
<211> LENGTH: 30
<212> TYPE: DNA
<213> ORGANISM: Homo sapien
<222> LOCATION: HUMvWFA31

<400> SEQUENCE: 40
ggacagatga taaatacata ggatggatgg　　　　　　　　　　　　30

<210> SEQ ID NO 41
<211> LENGTH: 24
<212> TYPE: DNA
<213> ORGANISM: Homo sapien
<222> LOCATION: HUMF13A01

<400> SEQUENCE: 41
gaggttgcac tccagccttt gcaa　　　　　　　　　　　　　　　　24

<210> SEQ ID NO 42
<211> LENGTH: 24
<212> TYPE: DNA
<213> ORGANISM: Homo sapien
<222> LOCATION: HUMF13A01

<400> SEQUENCE: 42
ttcctgaatc atcccagagc caca　　　　　　　　　　　　　　　　24

<210> SEQ ID NO 43
<211> LENGTH: 23
<212> TYPE: DNA
<213> ORGANISM: Homo sapien
<222> LOCATION: HUMFESFPS

<400> SEQUENCE: 43
gctgttaatt catgtaggga agg　　　　　　　　　　　　　　　　23

<210> SEQ ID NO 44
<211> LENGTH: 24
<212> TYPE: DNA
<213> ORGANISM: Homo sapien
<222> LOCATION: HUMFESFPS

<400> SEQUENCE: 44
gtagtcccag ctacttggct actc　　　　　　　　　　　　　　　　24

<210> SEQ ID NO 45
<211> LENGTH: 20
<212> TYPE: DNA
<213> ORGANISM: Homo sapien
<222> LOCATION: HUMBFXIII

<400> SEQUENCE: 45
tgaggtggtg tactaccata　　　　　　　　　　　　　　　　　　　20

```
<210> SEQ ID NO 46
<211> LENGTH: 20
<212> TYPE: DNA
<213> ORGANISM: Homo sapien
<222> LOCATION: HUMBFXIII

<400> SEQUENCE: 46
gatcatgcca ttgcactcta                                          20

<210> SEQ ID NO 47
<211> LENGTH: 24
<212> TYPE: DNA
<213> ORGANISM: Homo sapien
<222> LOCATION: HUMLIPOL

<400> SEQUENCE: 47
ctgaccaagg atagtgggat atag                                     24

<210> SEQ ID NO 48
<211> LENGTH: 23
<212> TYPE: DNA
<213> ORGANISM: Homo sapien
<222> LOCATION: HUMLIPOL

<400> SEQUENCE: 48
ggtaactgag cgagactgtg tct                                      23

<210> SEQ ID NO 49
<211> LENGTH: 18
<212> TYPE: DNA
<213> ORGANISM: Homo sapien
<222> LOCATION: D3S1539

<400> SEQUENCE: 49 ccacccttc agcaccag                                             18

<210> SEQ ID NO 50
<211> LENGTH: 20
<212> TYPE: DNA
<213> ORGANISM: Homo sapien
<222> LOCATION: D19S253

<400> SEQUENCE: 50
atagacagac agacggactg                                          20

<210> SEQ ID NO 51
<211> LENGTH: 19
<212> TYPE: DNA
<213> ORGANISM: Homo sapien
<222> LOCATION: D19S253

<400> SEQUENCE: 51
gggagtggag attacccct                                           19

<210> SEQ ID NO 52
<211> LENGTH: 21
<212> TYPE: DNA
<213> ORGANISM: Homo sapien
<222> LOCATION: D20S481

<400> SEQUENCE: 52
aaagctctct gaagcaggtg t                                        21

<210> SEQ ID NO 53
```

-continued

```
<211> LENGTH: 24
<212> TYPE: DNA
<213> ORGANISM: Homo sapien
<222> LOCATION: D20S481

<400> SEQUENCE: 53
cagattgcac tagaaagaga ggaa                                              24

<210> SEQ ID NO 54
<211> LENGTH: 23
<212> TYPE: DNA
<213> ORGANISM: Homo sapien
<222> LOCATION: D10S1239

<400> SEQUENCE: 54
caccctgtcc ccagctatct gga                                               23

<210> SEQ ID NO 55
<211> LENGTH: 27
<212> TYPE: DNA
<213> ORGANISM: Homo sapien
<222> LOCATION: D9S930

<400> SEQUENCE: 55
agttgaatct tgagtctctc agagtca                                           27

<210> SEQ ID NO 56
<211> LENGTH: 24
<212> TYPE: DNA
<213> ORGANISM: Homo sapien
<222> LOCATION: D4S2368

<400> SEQUENCE: 56
tgtactcatt ttcccgcaat gatg                                              24

<210> SEQ ID NO 57
<211> LENGTH: 24
<212> TYPE: DNA
<213> ORGANISM: Homo sapien
<222> LOCATION: D4S2368

<400> SEQUENCE: 57
tcagaaagta gggtctgggc tctt                                              24

<210> SEQ ID NO 58
<211> LENGTH: 28
<212> TYPE: DNA
<213> ORGANISM: Homo sapien
<222> LOCATION: D16S539

<400> SEQUENCE: 58
tgtgcatctg taagcatgta tctatcat                                          28

<210> SEQ ID NO 59
<211> LENGTH: 32
<212> TYPE: DNA
<213> ORGANISM: Homo sapien
<222> LOCATION: HUMvWFA31

<400> SEQUENCE: 59
gaaagcccta gtggatgata agaataatca gt                                     32

<210> SEQ ID NO 60
<211> LENGTH: 33
<212> TYPE: DNA
```

-continued

<213> ORGANISM: Homo sapien
<222> LOCATION: HUMvWFA31

<400> SEQUENCE: 60
ggacagatga taaatacata ggatggatgg ata                33

<210> SEQ ID NO 61
<211> LENGTH: 25
<212> TYPE: DNA
<213> ORGANISM: Homo sapien
<222> LOCATION: D9S930

<400> SEQUENCE: 61
gctatgggaa ttacaagcag gaaac                25

<210> SEQ ID NO 62
<211> LENGTH: 20
<212> TYPE: DNA
<213> ORGANISM: Homo sapien
<222> LOCATION: D18S51

<400> SEQUENCE: 62
ttcttgagcc cagaaggtta                20

<210> SEQ ID NO 63
<211> LENGTH: 24
<212> TYPE: DNA
<213> ORGANISM: Homo sapien
<222> LOCATION: D18S51

<400> SEQUENCE: 63
ctaccagcaa caacacaaat aaac                24

<210> SEQ ID NO 64
<211> LENGTH: 22
<212> TYPE: DNA
<213> ORGANISM: Homo sapien
<222> LOCATION: D21S11

<400> SEQUENCE: 64
atatgtgagt caattcccca ag                22

<210> SEQ ID NO 65
<211> LENGTH: 26
<212> TYPE: DNA
<213> ORGANISM: Homo sapien
<222> LOCATION: D21S11

<400> SEQUENCE: 65
tgtattagtc aatgttctcc agagac                26

<210> SEQ ID NO 66
<211> LENGTH: 21
<212> TYPE: DNA
<213> ORGANISM: Homo sapien
<222> LOCATION: HUMTH01

<400> SEQUENCE: 66
gtgattccca ttggcctgtt c                21

<210> SEQ ID NO 67
<211> LENGTH: 22
<212> TYPE: DNA
<213> ORGANISM: Homo sapien
<222> LOCATION: HUMTH01

```
<400> SEQUENCE: 67
attcctgtgg gctgaaaagc tc                                              22

<210> SEQ ID NO 68
<211> LENGTH: 19
<212> TYPE: DNA
<213> ORGANISM: Homo sapien
<222> LOCATION: D3S1358

<400> SEQUENCE: 68
gcagtccaat ctgggtgac                                                  19

<210> SEQ ID NO 69
<211> LENGTH: 20
<212> TYPE: DNA
<213> ORGANISM: Homo sapien
<222> LOCATION: D3S1358

<400> SEQUENCE: 69
atgaaatcaa cagaggcttg                                                 20

<210> SEQ ID NO 70
<211> LENGTH: 20
<212> TYPE: DNA
<213> ORGANISM: Homo sapien
<222> LOCATION: HUMFIBRA

<400> SEQUENCE: 70
ggctgcaggg cataacatta                                                 20

<210> SEQ ID NO 71
<211> LENGTH: 22
<212> TYPE: DNA
<213> ORGANISM: Homo sapien
<222> LOCATION: HUMFIBRA

<400> SEQUENCE: 71
tctatgactt tgcgcttcag ga                                              22

<210> SEQ ID NO 72
<211> LENGTH: 20
<212> TYPE: DNA
<213> ORGANISM: Homo sapien
<222> LOCATION: HUMTPOX

<400> SEQUENCE: 72
gcacagaaca ggcacttagg                                                 20

<210> SEQ ID NO 73
<211> LENGTH: 18
<212> TYPE: DNA
<213> ORGANISM: Homo sapien
<222> LOCATION: HUMTPOX

<400> SEQUENCE: 73
cgctcaaacg tgaggttg                                                   18

<210> SEQ ID NO 74
<211> LENGTH: 32
<212> TYPE: DNA
<213> ORGANISM: Homo sapien
<222> LOCATION: D8S1179

<400> SEQUENCE: 74
```

```
attgcaactt atatgtattt ttgtatttca tg                              32

<210> SEQ ID NO 75
<211> LENGTH: 28
<212> TYPE: DNA
<213> ORGANISM: Homo sapien
<222> LOCATION: D8S1179

<400> SEQUENCE: 75
accaaattgt gttcatgagt atagtttc                                   28

<210> SEQ ID NO 76
<211> LENGTH: 33
<212> TYPE: DNA
<213> ORGANISM: Homo sapien
<222> LOCATION: HUMvWFA31

<400> SEQUENCE: 76
gccctagtgg atgataagaa taatcagtat gtg                             33

<210> SEQ ID NO 77
<211> LENGTH: 24
<212> TYPE: DNA
<213> ORGANISM: Homo sapien
<222> LOCATION: HUMCSF1PO

<400> SEQUENCE: 77
ccggaggtaa aggtgtctta aagt                                       24

<210> SEQ ID NO 78
<211> LENGTH: 22
<212> TYPE: DNA
<213> ORGANISM: Homo sapien
<222> LOCATION: HUMCSF1PO

<400> SEQUENCE: 78
atttcctgtg tcagaccctg tt                                         22

<210> SEQ ID NO 79
<211> LENGTH: 29
<212> TYPE: DNA
<213> ORGANISM: Homo sapien
<222> LOCATION: D16S539

<400> SEQUENCE: 79
gtttgtgtgt gcatctgtaa gcatgtatc                                  29

<210> SEQ ID NO 80
<211> LENGTH: 21
<212> TYPE: DNA
<213> ORGANISM: Homo sapien
<222> LOCATION: D7S820

<400> SEQUENCE: 80
atgttggtca ggctgactat g                                          21

<210> SEQ ID NO 81
<211> LENGTH: 24
<212> TYPE: DNA
<213> ORGANISM: Homo sapien
<222> LOCATION: D7S820

<400> SEQUENCE: 81
gattccacat ttatcctcat tgac                                       24
```

<210> SEQ ID NO 82
<211> LENGTH: 26
<212> TYPE: DNA
<213> ORGANISM: Homo sapien
<222> LOCATION: D13S317

<400> SEQUENCE: 82
attacagaag tctgggatgt ggagga                                26

<210> SEQ ID NO 83
<211> LENGTH: 19
<212> TYPE: DNA
<213> ORGANISM: Homo sapien
<222> LOCATION: D13S317

<400> SEQUENCE: 83
ggcagcccaa aaagacaga                                       19

<210> SEQ ID NO 84
<211> LENGTH: 23
<212> TYPE: DNA
<213> ORGANISM: Homo sapien
<222> LOCATION: D5S818

<400> SEQUENCE: 84
ggtgattttc ctctttggta tcc                                  23

<210> SEQ ID NO 85
<211> LENGTH: 26
<212> TYPE: DNA
<213> ORGANISM: Homo sapien
<222> LOCATION: D5S818

<400> SEQUENCE: 85
agccacagtt tacaacattt gtatct                               26

<210> SEQ ID NO 86
<211> LENGTH: 19
<212> TYPE: DNA
<213> ORGANISM: Homo sapien
<222> LOCATION: Amelogenin

<400> SEQUENCE: 86
ccctgggctc tgtaaagaa                                       19

<210> SEQ ID NO 87
<211> LENGTH: 24
<212> TYPE: DNA
<213> ORGANISM: Homo sapien
<222> LOCATION: Amelogenin

<400> SEQUENCE: 87
atcagagctt aaactgggaa gctg                                 24

<210> SEQ ID NO 88
<211> LENGTH: 24
<212> TYPE: DNA
<213> ORGANISM: Homo sapien
<222> LOCATION: G475

<400> SEQUENCE: 88
taccaacatg aaagggtacc aata                                 24

-continued

<210> SEQ ID NO 89
<211> LENGTH: 27
<212> TYPE: DNA
<213> ORGANISM: Homo sapien
<222> LOCATION: G475

<400> SEQUENCE: 89
tgggttatta attgagaaaa ctcctta                                27

<210> SEQ ID NO 90
<211> LENGTH: 20
<212> TYPE: DNA
<213> ORGANISM: Homo sapien
<222> LOCATION: S159

<400> SEQUENCE: 90
gccatgatca caccactaca                                       20

<210> SEQ ID NO 91
<211> LENGTH: 26
<212> TYPE: DNA
<213> ORGANISM: Homo sapien
<222> LOCATION: S159

<400> SEQUENCE: 91 ccgatttttta attgggttgt cttatt                               26

<210> SEQ ID NO 92
<211> LENGTH: 23
<212> TYPE: DNA
<213> ORGANISM: Homo sapien
<222> LOCATION: S159

<400> SEQUENCE: 92
gccatgatca caccactaca ctc                                   23

<210> SEQ ID NO 93
<211> LENGTH: 24
<212> TYPE: DNA
<213> ORGANISM: Homo sapien
<222> LOCATION: S159

<400> SEQUENCE: 93 ccgatttttta attgggttgt ctta                                 24

<210> SEQ ID NO 94
<211> LENGTH: 33
<212> TYPE: DNA
<213> ORGANISM: Homo sapien
<222> LOCATION: G475

<400> SEQUENCE: 94
tgggttatta attgagaaaa ctccttacaa ttt                        33

<210> SEQ ID NO 95
<211> LENGTH: 22
<212> TYPE: DNA
<213> ORGANISM: Homo sapien
<222> LOCATION: S159

<400> SEQUENCE: 95
gcacagtggc taattgtacc tt                                    22

<210> SEQ ID NO 96
<211> LENGTH: 26

```
<212> TYPE: DNA
<213> ORGANISM: Homo sapien
<222> LOCATION: S159

<400> SEQUENCE: 96
tttttaatag gtcatgattt tgtgat                                          26

<210> SEQ ID NO 97
<211> LENGTH: 24
<212> TYPE: DNA
<213> ORGANISM: Homo sapien
<222> LOCATION: D16S539

<400> SEQUENCE: 97
gtttgtgtgt gcatctgtaa gcat                                            24

<210> SEQ ID NO 98
<211> LENGTH: 24
<212> TYPE: DNA
<213> ORGANISM: Homo sapien
<222> LOCATION: HUMCSF1PO

<400> SEQUENCE: 98
cctgtgtcag accctgttct aagt                                            24

<210> SEQ ID NO 99
<211> LENGTH: 25
<212> TYPE: DNA
<213> ORGANISM: Homo sapien
<222> LOCATION: C221

<400> SEQUENCE: 99
aacagggata tgcactggta ataga                                           25

<210> SEQ ID NO 100
<211> LENGTH: 21
<212> TYPE: DNA
<213> ORGANISM: Homo sapien
<222> LOCATION: C221

<400> SEQUENCE: 100
tgcataaaac cctggttggt c                                               21

<210> SEQ ID NO 101
<211> LENGTH: 20
<212> TYPE: DNA
<213> ORGANISM: Homo sapien
<222> LOCATION: D18S51

<400> SEQUENCE: 101
caaacccgac taccagcaac                                                 20

<210> SEQ ID NO 102
<211> LENGTH: 20
<212> TYPE: DNA
<213> ORGANISM: Homo sapien
<222> LOCATION: D18S51

<400> SEQUENCE: 102
gagccatgtt catgccactg                                                 20

<210> SEQ ID NO 103
<211> LENGTH: 24
<212> TYPE: DNA
<213> ORGANISM: Homo sapien
```

-continued

```
<222> LOCATION: HUMTHO1

<400> SEQUENCE: 103
gtgattccca ttggcctgtt cctc                                            24

<210> SEQ ID NO 104
<211> LENGTH: 28
<212> TYPE: DNA
<213> ORGANISM: Homo sapien
<222> LOCATION: D8S1179

<400> SEQUENCE: 104
tggcaactta tatgtatttt gtatttc                                         28

<210> SEQ ID NO 105
<211> LENGTH: 24
<212> TYPE: DNA
<213> ORGANISM: Homo sapien
<222> LOCATION: Amelogenin

<400> SEQUENCE: 105
ccctgggctc tgtaaagaat agtg                                            24

<210> SEQ ID NO 106
<211> LENGTH: 19
<212> TYPE: DNA
<213> ORGANISM: Homo sapien
<222> LOCATION: D3S1358

<400> SEQUENCE: 106
actgcagtcc aatctgggt                                                  19

<210> SEQ ID NO 107
<211> LENGTH: 21
<212> TYPE: DNA
<213> ORGANISM: Homo sapien
<222> LOCATION: HUMFIBRA

<400> SEQUENCE: 107
ctatgacttt gcgcttcagg a                                               21

<210> SEQ ID NO 108
<211> LENGTH: 1000
<212> TYPE: DNA
<213> ORGANISM: Homo sapien
<220> FEATURE:
<222> LOCATION: Clone S159
<223> OTHER INFORMATION: from a pGem3Zf(+)plasmid library

<400> SEQUENCE: 108 aaacccgtc tctactaaaa atacaaaagt tagttgagca tggtggcacg                  50
ggcctgtaat cccacctata atcccaccta ctcgggaggc tgaggcagga                 100
gaatcgcttg aacccaggat ggggcgattg cagtgagccg agatcgtgcc                 150
actgcactcc agcctgggtg acagagcgag actccatctc aaaaaaaaaa                 200
aaaaaaaaca gaatcatagg ccaggcacag tggctaattg taccttggga                 250
ggctgagacg ggaggatcga gaccatcctg ggcaccatag tgagacccca                 300
tctctacaaa aaaaaaaaaa aatttttttt aaatagccag gcatggtgag                 350
gctgaagtag gatcacttga gcctggaagg tcgaagctga agtgagccat                 400
gatcacacca ctacactcca gcctaggtga cagagcaaga caccatctca                 450
```

-continued

| | |
|---|---|
| agaaagaaaa aaaagaaaga aaagaaaaga aaagaaaaga aaagaaaaga | 500 |
| aaagaaaaga aaaaacgaag gggaaaaaaa gagaatcata aacataaatg | 550 |
| taaaatttct caaaaaaatc gttatgacca taggttaggc aaatatttct | 600 |
| tagatatcac aaaatcatga cctattaaaa aataataata agtaagttt | 650 |
| catcaaaact taaaagttct actcttcaaa agataccta taaagaaagt | 700 |
| aaaaagacac gccacaggct aagagaaagt acttctaatc acatatctaa | 750 |
| aaaaggactt gtgtccagat taaagaattc ttacacatca ataagacaac | 800 |
| ccaattaaaa atcggcaaaa gatttgaaga gatatttaac caaagaaaac | 850 |
| atataaatgt gtccgggcgc gatggtaatc ccagcacttt gagaggccga | 900 |
| ggcaggcgga tcacttgagg tcaggagttt aggaccagtc tggccaacat | 950 |
| ggtgaaaccc tgtctctaat aaaaatacaa aaattagctg ggtgtggtgg | 1000 |

<210> SEQ ID NO 109
<211> LENGTH: 411
<212> TYPE: DNA
<213> ORGANISM: Homo sapien
<220> FEATURE:
<222> LOCATION: Clone C221
<223> OTHER INFORMATION: from a pGem3Zf(+)plasmid library

<400> SEQUENCE: 109

| | |
|---|---|
| gatcacttgc catccctgcc acacagtttc ctcctctgga aactgggggt | 50 |
| gatgacccct gccctaccca cttgtcatgg cattggggac atgaacacac | 100 |
| tttgcacctg tcaggcaagg cttaaacagg gatatgcact ggtaatagaa | 150 |
| aagagggact aagttttgtt ttgttttgtt ttgttttgtt ttgttttgtt | 200 |
| ttgttttgtt ttgttttgtt ttgtttttct gaagaagtcc ctagaagcgc | 250 |
| tcagtgttgg aatgctctct tgtagcagtg gcggctgctg ctggttccgg | 300 |
| gtcagatgcc ggaattgggg gtgcgcttgg gtgcagctgc atttcatctg | 350 |
| gtcctgggcc tcggtcctgg cttggagagg tgcagctcac agccacttca | 400 |
| tggctgggat c | 411 |

<210> SEQ ID NO 110
<211> LENGTH: 335
<212> TYPE: DNA
<213> ORGANISM: Homo sapien
<220> FEATURE:
<222> LOCATION: Clone G475
<223> OTHER INFORMATION: from a pGem3Zf(+)plasmid library

<400> SEQUENCE: 110

| | |
|---|---|
| gatcacgcca ttgcactcca gcctgggcga ctgagcaaga ctcagtctca | 50 |
| aagaaaagaa aagaaaagaa aagaaaagaa aagaaaagaa aagaaaagaa | 100 |
| aagaaaagaa aattgtaagg agttttctca attaataacc caaataagag | 150 |
| aattctttcc atgtatcaat catgatacta agcactttac acacatgtat | 200 |
| gttatgtaat cattatatca tgcatgcaag gtaatgagta ttattttcct | 250 |
| cattttataa aagaggaaac tgatgtttga ggctactttg cttaagaccg | 300 |
| cagaactagc aaaggaaaag agaagtgaat gtatc | 335 |

MULTIPLEX AMPLIFICATION OF SHORT TANDEM REPEAT LOCI

CROSS-REFERENCE TO RELATED APPLICATIONS

This application is a divisional of U.S. patent application Ser. No. 09/199,542, filed Nov. 25, 1998, now U.S. Pat. No. 6,479,235, issued Nov. 12, 2002, which is a continuation-in-part of U.S. patent application Ser. No. 08/632,575, filed Apr. 15, 1996, now U.S. Pat. No. 5,843,660, issued Dec. 1, 1998, which is a continuation-in-part of U.S. patent application Ser. No. 08/316,544, filed Sep. 30, 1994, now abandoned.

STATEMENT REGARDING FEDERALLY SPONSORED RESEARCH OR DEVELOPMENT

Not applicable.

FIELD OF THE INVENTION

The present invention is generally directed to the detection of genetic markers in a genomic system. The present invention is more specifically directed to the simultaneous amplification of multiple distinct polymorphic genetic loci using the polymerase chain reaction or other amplification systems to determine, in one reaction, the alleles of each locus contained within the multiplex system.

BACKGROUND OF THE INVENTION

DNA typing is commonly used to identify the parentage of human children, and to confirm the lineage of horses, dogs, other animals, and agricultural crops. DNA typing is also commonly employed to identify the source of blood, saliva, semen, and other tissue found at a crime scenes or other sites requiring identification of human remains. DNA typing is also employed in clinical settings to determine success or failure of bone marrow transplantation and presence of particular cancerous tissues. DNA typing involves the analysis of alleles of genomic DNA with characteristics of interest, commonly referred to as "markers". Most typing methods in use today are specifically designed to detect and analyze differences in the length and/or sequence of one or more regions of DNA markers known to appear in at least two different forms in a population. Such length and/or sequence variation is referred to as "polymorphism." Any region (i.e. "locus") of DNA in which such a variation occurs is referred to as a "polymorphic locus." The methods and materials of the present invention are designed for use in the detection of multiple loci of DNA, some or all of which are polymorphic loci.

Genetic markers which are sufficiently polymorphic with respect to length or sequence have long been sought for use in identity applications, such as paternity testing and identification of tissue samples collected for forensic analysis. The discovery and development of such markers and methods for analyzing such markers have gone through several phases of development over the last several years.

The first identified DNA variant markers were simple base substitutions, i.e. simple sequence polymorphisms, which were most often detected by Southern hybridization assays. For examples of references describing the identification of such markers, designed to be used to analyze restriction endonuclease-digested DNA with radioactive probes, see: Southern, E. M. (1975), *J. Mol. Biol.* 98(3):503–507; Schumm, et al. (1988), *American Journal of Human Genetics* 42:143–159; and Wyman, A. and White, R. (1980) *Proc. Natl. Acad. Sci, U.S.A.* 77:6754–6758.

The next generation of markers were size variants, i.e. length polymorphisms, specifically "variable number of tandem repeat" (VNTR) markers (Nakamura Y., et al. (1987), *Science* 235: 1616–1622; and U.S. Pat. No. 4,963,663 issued to White et al. (1990); U.S. Pat. No. 5,411,859 continuation of 4,963,663 issued to White et al. (1995)) and "minisatellite" markers (Jeffreys et al. (1985a), *Nature* 314: 67–73; Jeffreys et al. (1985b) *Nature* 316:76–79, U.S. Pat. No. 5,175,082 for an invention by Jeffreys). Both VNTR and minisatellite markers, contain regions of nearly identical sequences repeated in tandem fashion. The core repeat sequence is 10 to 70 bases in length, with shorter core repeat sequences referred to as "minisatellite" repeats and longer repeats referred to as VNTRs. Different individuals in a human population contain different numbers of the repeats. The VNTR markers are generally more highly polymorphic than base substitution polymorphisms, sometimes displaying up to forty or more alleles at a single genetic locus. However, the tedious process of restriction enzyme digestion and subsequent Southern hybridization analysis are still required to detect and analyze most such markers.

The next advance involved the joining of the polymerase chain reaction (PCR) (U.S. Pat. No. 4,683,202 by Mullis, K. B.) technology with the analysis of VNTR loci (Kasai, K. et al. (1990) *Journal Forensic Science* 35(5):1196–1200). Amplifiable VNTR loci were discovered, which could be detected without the need for Southern transfer. The amplified products are separated through agarose or polyacrylamide gels and detected by incorporation of radioactivity during the amplification or by post-staining with silver or ethidium bromide. However, PCR can only be used to amplify relatively small DNA segments reliably, i.e. only reliably amplifying DNA segments under 3,000 bases in length Ponce, M & Micol, L. (1992) *NAR* 20(3):623; Decorte R, et al. (1990) *DNA Cell Biol.* 9(6):461–469). Consequently, very few amplifiable VNTRs have been developed.

In recent years, the discovery and development of polymorphic short tandem repeats (STRs) as genetic markers has stimulated progress in the development of linkage maps, the identification and characterization of diseased genes, and the simplification and precision of DNA typing. Specifically, with the discovery and development of polymorphic markers containing dinucleotide repeats (Litt and Luty (1989) *Am J. Hum Genet* 3(4):599–605; Tautz, D (1989) *NAR* 17:6463–6471; Weber and May (1989) *Am J Hum Genet* 44:388–396; German Pat. No. DE 38 34 636 C2, inventor Tautz, D; U.S. Pat. No. 5,582,979 filed by Weber, L.), STRs with repeat units of three to four nucleotides (Edwards, A., et al. (1991) *Am. J. Hum. Genet.* 49: 746–756.; Hammond, H. A., et al. (1994) *Am. J. Hum. Genet.* 55: 175–189; Fregeau, C. J.; and Fourney, R. M. (1993) *BioTechniques* 15(1): 100–119.; Schumm, J. W. et al. (1994) in *The Fourth International Symposium on Human Identification* 1993, pp. 177–187 (pub. by Promega Corp., 1994); and U.S. Pat. No. 5,364,759 by Caskey et al.; German Pat. No. DE 38 34 636 C2 by Tautz, D.) and STRs with repeat units of five to seven bases (See, e.g. Edwards et al. (1991) *Nucleic Acids Res.* 19:4791; Chen et al. (1993) *Genomics* 15(3): 621–5; Harada et al. (1994) *Am. J. Hum. Genet.* 55: 175–189; Comings et al. (1995), *Genomics* 29(2):390–6; and Utah Marker Development Group (1995), *Am. J. Genet.* 57:619–628; and Jurka and Pethiyagoda (1995) *J. Mol. Evol.* 40:120–126)), many of the deficiencies of previous methods have been overcome. STR markers are generally shorter than VNTR markers, making them better substrates for amplification than most VNTR markers.

STR loci are similar to amplifiable VNTR loci in that the amplified alleles at each such locus may be differentiated based on length variation. Generally speaking STR loci are less polymorphic at each individual locus than VNTR loci. Thus, it is desirable to amplify and detect multiple STR systems in a single amplification reaction and separation to provide information for several loci simultaneously. Systems containing several loci are called multiplex systems and many such systems containing up to 11 separate STR loci have been described. See, e.g., *Proceedings: American Academy of Forensic Sciences* (Feb. 9–14, 1998), Schumm, James W. et al., p. 53, B88; Id., Gibson, Sandra D. et al., p. 53, B89; Id., Lazaruk, Katherine et al., p. 51, B83; Sparkes, R. et al., *Int J Legal Med* (1996) 109:186–194; *AmpFlSTR Profiler™ PCR Amplification Kit User's Manual* (1997), pub by Perkin-Elmer Corp, i–viii and 1—1 to 1–10; *AmpFlSTR Profiler Plus™ PCR Amplification Kit User's Manual* (1997), pub by Perkin-Elmer Corp., i viii and 1—1 to 1–10; *AmpFlSTR COfiler™ PCR Amplification Kit User Bulletin* (1998), pub by Perkin-Elmer Corp. i–iii and 1—1 to 1–10; *9th International Symposium on Human Identification* (Oct. 7–10, 1998), pub. by Promega Corp., Staub, Rick W. et al., Poster Abstract 15; Id., Willard, Jeanne M. et al., Poster Abstract 73; and Id., Walsh, P. Sean, et al., Speaker Abstract for 8:50 am–9:20 am, Thursday, Oct. 8, 1998.

Amplification protocols with STR loci can be designed to produce small products, generally from 60 to 500 base pairs (bp) in length, and alleles from each locus are often contained within a range of less than 100 bp. This allows simultaneous electrophoretic analysis of several systems on the same gel or capillary electrophoresis by careful design of PCR primers such that all potential amplification products from an individual system do not overlap the range of alleles of other systems. Design of these systems is limited, in part, by the difficulty in separating multiple loci in a single gel or capillary. This occurs because there is spacial compression of fragments of different sizes, especially longer fragments in gels or capillaries, i.e., commonly used means for separation of DNA fragments by those skilled in the art.

The United States Federal Bureau of Investigation ("FBI") has established and maintains a Combined DNA Index System ("CODIS"), a database of DNA typing information. Local, state, and national law enforcement agencies use the CODIS system to match forensic DNA evidence collected at crime scenes with DNA information in the database. CODIS and other national database systems have proven to be an effective tool for such agencies to use in solving violent crimes. (See, e.g. Niezgoda, Stephen, in *Cambridge Healthtech Institute's Second Annual Conference on DNA Forensics: Science, Evidence, and Future Prospects* (Nov. 17–18, 1998), pp. 1–21.; Niezgoda, Stephen in *Proceedings From The Eighth International Symposium on Human Identification* 1997, pub. by Promega Corporation (1998), pp 48–49; Frazier, Rachel R. E. et al. Id., pp. 56–60; Niezgoda, S. J. *Profiles in DNA* 1(3): 12–13; Werrett, D. J. and Sparkes, R. in *Speaker Abstracts: 9th International Symposium on Human Identification* (Oct. 7–10, 1998) pp. 5–6). Until recently, only restriction fragment length polymorphism ("RFLP") data obtained from the analysis of particular VNTR loci was considered a core component in the database. The FBI has recently identified thirteen polymorphic STR loci for inclusion in the CODIS database. The thirteen CODIS STR loci are HUMCSF1PO, D3S1358, D5S818, D7S820, D8S1179, D13S317, D16S539, D18S51, D21S11, HUMFIBRA, HUMTH01, HUMTPOX, and HUMvWFA31. (Budowle, Bruce and Moretti, Tamyra in *Speaker Abstracts: 9th International Symposium on Human Identification* (Oct. 7–10, 1998) pp. 7–8). Both VNTR and STR marker data are currently maintained in the CODIS database. (See, e.g. Niezgoda, Stephen in *Second Annual Conference on DNA Forensics*, supra). Until the present invention, the number of loci which could be co-amplified in a single reaction, and analyzed thereafter was limited. Specifically, no materials or methods had been developed for use in multiplex amplification of thirteen or more STR loci, much less the thirteen polymorphic STR loci identified for use in the CODIS database.

The materials and methods of the present method are designed for use in multiplex analysis of particular polymorphic loci of DNA of various types, including single-stranded and double-stranded DNA from a variety of different sources. The present invention represents a significant improvement over existing technology, bringing increased power of discrimination, precision, and throughput to DNA profiling for linkage analysis, criminal justice, paternity testing, and other forensic, medical, and genetic identification applications.

SUMMARY OF THE INVENTION

It is, therefore, an object of the present invention to provide a method and materials for the simultaneous amplification of sets of loci, which include multiple distinct polymorphic short tandem repeat (STR) loci, in a single multiplex reaction, using PCR or other amplification systems in combination with gel electrophoresis, capillary electrophoresis or other separation and detection methods to analyze and compare the relative lengths of the alleles of each locus amplified in the multiplex reaction. Multiplex analysis of the sets of loci disclosed herein has not been previously described in the prior art. There has also not been any previous description of the sequences for many of the primers disclosed herein below, all of which are shown to be useful in multiplex amplification of the sets of loci disclosed.

It is also an object of the present invention to provide a method, a kit, and primers specific for multiplex amplifications comprising specified loci.

These and other objects are addressed by the present invention which is directed to a method and materials for simultaneously analyzing or determining the alleles present at each individual locus of each multiplex. In general, the method of this invention comprises the steps of (a) obtaining at least one DNA sample to be analyzed, wherein the DNA sample has at least thirteen loci which can be co-amplified; (b) co-amplifying the at least thirteen loci of the DNA sample; and (c) detecting the amplified materials in a fashion which reveals the polymorphic nature of the systems employed.

In one embodiment, the present invention is a method of simultaneously determining the alleles present in a set of loci from one or more DNA samples, comprising the steps of:

(a) obtaining at least one DNA sample to be analyzed;

(b) selecting a set of loci of the DNA sample, comprising at least thirteen short tandem repeat loci which can be co-amplified;

(c) co-amplifying the loci in the set in a multiplex amplification reaction, wherein the product of the reaction is a mixture of amplified alleles from each of the co-amplified loci in the set; and (d) evaluating the amplified alleles in the mixture to determine the alleles present at each of the loci analyzed in the set within the DNA sample.

At least four of the at least thirteen short tandem repeat loci are preferably selected from the group of loci consisting of: D3S1539, D4S2368, D5S818, D7S820, D9S930, D10S1239, D13S317, D14S118, D14S548, D14S562, D16S490, D16S539, D16S753, D17S1298, D17S1299, D19S253, D20S481, D22S683, HUMCSF1PO, HUMTPOX, HUMTH01, HUMF13AO1, HUMBFXIII, HUMLIPOL, HUMvWFA31.

In another embodiment of the invention, the set of loci selected in step (b) of In another embodiment of the invention, the set of loci selected in step (b) of the method comprises thirteen CODIS STR loci (i.e., D3S1358, D5S818, D7S820, D8S1179, D13S317, D16S539, D18S51, D21S11, HUMCSF1PO, HUMFIBRA, HUMTH01, HUMTPOX, and HUMvWFA31) which can be co-amplified and analyzed by themselves, or with additional loci using methods of the present invention.

In a further aspect, this invention is a kit for simultaneously analyzing a set of loci of genomic DNA, comprising oligonucleotide primers for co-amplifying a set of loci of the genomic DNA to be analyzed, wherein the set of loci comprises at least thirteen short tandem repeat loci which can be co-amplified in the same multiplex reaction, and wherein the primers are in one or more containers. More preferably, the kit comprises oligonucleotide primer pairs for co-amplifying a set of at least thirteen loci of human genomic DNA, the set of loci comprising D3S1358, D5S818, D7S820, D8S1179, D13S317, D16S539, D18S51, D21S11, HUMCSF1PO, HUMFIBRA, HUMTH01, HUMTPOX, and HUMvWFA31.

In yet a further aspect, the invention is primer sequences and primer pairs for amplifying specific loci of human DNA. Use of the primers and primer pairs of this invention for multiplex analysis of human DNA is demonstrated herein, below. The primers of this invention are suitable for use in the method of this invention, wherein they can be used in labeled form, as noted below, to assist the evaluation step of the method.

The approaches specified in the present invention produce savings of time, labor, and materials in the analysis of loci contained within the multiplexes. The method of the present invention allows thirteen or more, even as many as sixteen or more, loci to be co-amplified in one tube using a single amplification reaction, instead of amplifying each locus independently in separate tubes or in smaller groups of loci.

The present invention has specific use in the field of forensic analysis, paternity determination, monitoring of bone marrow transplantation, linkage mapping, and detection of genetic diseases and cancers. By allowing thirteen methods of the present invention significantly increase the certainty with which one can match DNA prepared from different samples from the same individual. The need to match or distinguish accurately between samples containing very small amounts of DNA is particularly acute in forensics applications, where many convictions (and acquittals) turn on DNA typing analysis.

Scientists, particularly forensic scientists, have long appreciated the need to analyze multiple polymorphic loci of DNA in order to ensure that a match between two samples of DNA is statistically significant. (Presley, L. A. et al., in *The Third International Symposium on Human Identification* 1992, pp. 245–269 (pub. by Promega Corp., 1993); Bever, R. A., et al., in *The Second International Symposium on Human Identification* 1991, pp. 103–128. (pub. by Promega Corp., 1992)) However, until this invention, one could not simultaneously analyze thirteen or more STR loci in a single reaction. To realize the importance of such multiplexing capabilities, it helps to understand some of the mathematics behind DNA typing analysis.

For purposes of illustration, suppose every STR locus has a genotype (i.e., pattern of two alleles) frequency of one in ten. In other words, suppose that the chance of two randomly selected individuals have a matching type for a single STR is 1/10. However, if two different STR loci are analyzed, the chance of a random match with both systems is 1/100. If three STR loci are analyzed, the chances of a random match with each of the three systems is 1/1,000 and so on. Consequently, it is easy to see how increasing the number of STR loci analyzed reduces the likelihood of random matches within the general population, thereby increasing the chance one can accurately identify a suspect's presence at a crime scene by comparing the individual's type with crime scene evidence. Similar reasoning can be used to conclude that the method of this invention also would increase the likelihood of accurately identifying a suspected father in a paternity case, of correctly matching bone marrow tissue, of developing significant results from linkage mapping studies, and of detecting genetic diseases and cancers.

Further objects, features, and advantages of the invention will be apparent from the following best mode for carrying out the invention and the illustrative drawings.

BRIEF DESCRIPTION OF THE DRAWINGS

FIGS. 4A and 4B are laser printed images of the results of fluorescent detection of the products of simultaneous amplification of the loci D3S1358, D5S818, D7S820, D8S1179, D13S317, D16S539, D18S51, D21S11, HUMCSF1PO, HUMFIBRA, HUMTH01, HUMTPOX, HUMvWFA31, G475, S159, and Amelogenin as detected using the fluorescein channel (FIG. 4A) and carboxy-tetramethylrhodamine channel (FIG. 4B) of a Hitachi FMBIO® II Fluorescent Scanner, as described in Example 4.

FIGS. 5A and 5B are laser printed images of the results of fluorescent detection of the products of simultaneous amplification of the loci D3S1358, D5S818, D7S820, D8S1179, D13S317, D16S539, D18S51, D21S11, HUMCSF1PO, HUMFIBRA, HUMTH01, HUMTPOX, HUMvWFA31, G475, S159, and Amelogenin as detected using the fluorescein channel (FIG. 5A) and carboxy-tetramethylrhodamine channel (FIG. 5B) of a Hitachi FMBIO® II Fluorescent Scanner, as described in Example 5.

DETAILED DESCRIPTION OF THE INVENTION

A. Definitions

Figure 1A:
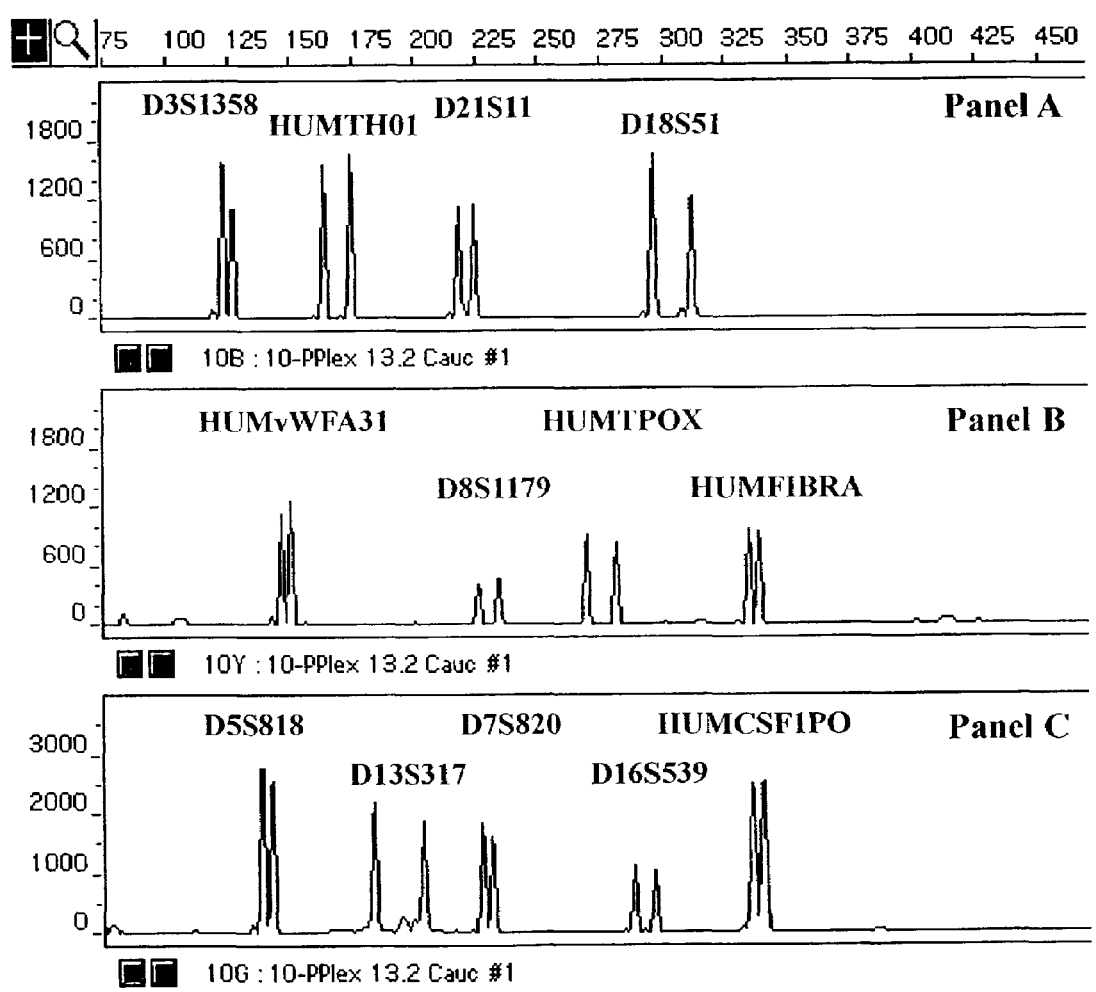
FIG. 1A is a plot of the output of three-color fluorescent detection of the products of simultaneous amplification of the loci D3S1358, D5S818, D7S820, D8S1179, D13S317, D16S539, D18S51, D21S11, HUMCSF1PO, HUMFIBRA, HUMTH01, HUMTPOX, and HUMvWFA31 of a sample of human genomic DNA, as detected with the ABI PRISM® 310 Genetic Analyzer in Example 1.

The following definitions are intended to assist in providing a clear and consistent understanding of the scope and detail of the following terms, as used to describe and define the present invention:

"Allelic ladder": a standard size marker consisting of amplified alleles from the locus.

"Allele": a genetic variation associated with a segment of DNA, i.e., one of two or more alternate forms of a DNA sequence occupying the same locus.

"Biochemical nomenclature": standard biochemical nomenclature is used herein in which the nucleotide bases are designated as adenine (A); thymine (T); guanine (G); and cytosine (C). Corresponding nucleotides are, for example, deoxyguanosine-5'-triphosphate (dGTP).

"DNA polymorphism": the condition in which two or more different nucleotide sequences in a DNA sequence coexist in the same interbreeding population.

"Locus" or "genetic locus": a specific position on a chromosome. Alleles of a locus are located at identical sites on homologous chromosomes.

"Locus-specific primer": a primer that specifically hybridizes with a portion of the stated locus or its complementary strand, at least for one allele of the locus, and does not hybridize efficiently with other DNA sequences under the conditions used in the amplification method.

"Pentanucleotide tandem repeat": a subclass of the STR polymorphisms defined below. Unless specified otherwise, the term "pentanucleotide tandem repeat" encompasses perfect STRs wherein the repeat unit is a five base sequence, and imperfect STRs wherein at least one repeat unit is a five base repeat.

"Polymerase chain reaction" or "PCR": a technique in which cycles of denaturation, annealing with primer, and extension with DNA polymerase are used to amplify the number of copies of a target DNA sequence by approximately $10^6$ times or more. The polymerase chain reaction process for amplifying nucleic acid is covered by U.S. Pat. Nos. 4,683,195 and 4,683,202, which are incorporated herein by reference for a description of the process.

"Polymorphic short tandem repeat loci": STR loci, defined below, in which the number of repetitive sequence elements (and net length of sequence) in a particular region of genomic DNA varies from allele to allele, and from individual to individual.

"Polymorphism information content" or "PIC": a measure of the amount of polymorphism present at a locus (Botstein et al., 1980). PIC values range from 0 to 1.0, with higher values indicating greater degrees of polymorphism. This measure generally displays smaller values than the other commonly used measure, i.e., heterozygosity. For markers that are highly informative (heterozygosities exceeding about 70%), the difference between heterozygosity and PIC is slight.

"Primer": a single-stranded oligonucleotide or DNA fragment which hybridizes with a DNA strand of a locus in such a manner that the 3' terminus of the primer may act as a site of polymerization using a DNA polymerase enzyme.

"Primer pair": two primers including, primer 1 that hybridizes to a single strand at one end of the DNA sequence to be amplified and primer 2 that hybridizes with the other end on the complementary strand of the DNA sequence to be amplified.

"Primer site": the area of the target DNA to which a primer hybridizes.

"Short tandem repeat loci" or "STR loci": regions of genomic DNA which contain short, repetitive sequence elements of 3 to 7 base pairs in length. The term STR also encompasses a region of genomic DNA wherein more than a single three to seven base sequence is repeated in tandem or with intervening bases, provided that at least one of the sequences is repeated at least two times in tandem. Each sequence repeated at least once within an STR is referred to herein as a "repeat unit."

The sequences of the STR loci analyzed using the materials and methods of the present invention can be divided into two general categories, perfect and imperfect. The term "perfect" STR, as used herein, refers to a region of double-stranded DNA containing a single three to seven base repeat unit repeated in tandem at least two times, e.g. $(AAAAT)_2$. The term "imperfect" STR, as used herein, refers to a region of DNA containing at least two tandem repeats of a perfect repeat unit and at least one repeat of an imperfect repeat unit, wherein the imperfect repeat unit consists of a DNA sequence which could result from one, two, three, or four base insertions, deletions, or substitutions in the sequence of the perfect repeat unit, e.g. $(AAAAT)_{12}(AAAAAT)_5AAT(AAATT)_4$. Every imperfect STR sequence contains at least one perfect STR sequence. Specifically, every STR sequence, whether perfect or imperfect, includes at least one repeat unit sequence appearing at least two times in tandem, a repeat unit sequence which can be represented by formula (I):

$$(A_2G_xT_yC_z)_n \tag{I}$$

wherein A, G, T, and C represent the nucleotides which can be in any order; w, x, y and z represent the number of each nucleotide in the sequence and range from 0 to 7 with the sum of w+x+y+z ranging between 3 and 7; and n represents the number of times the sequence is tandemly repeated and is at least 2.

B. Selection of Multiplex Reaction Components

The method of the present invention contemplates selecting an appropriate set of loci, primers, and amplification protocols to generate amplified alleles from multiple co-amplified loci which preferably do not overlap in size or, more preferably, which are labeled in a way which enables one to differentiate between the alleles from different loci which overlap in size. In addition, this method contemplates the selection of short tandem repeat loci which are compatible for use with a single amplification protocol. The specific combinations of loci described herein are unique in this application. Combinations of loci may be rejected for either of the above two reasons, or because, in combination, one or more of the loci do not produce adequate product yield, or fragments which do not represent authentic alleles are produced in this reaction.

Successful combinations in addition to those disclosed herein can be generated by trial and error of locus combinations, by selection of primer pair sequences, and by adjustment of primer concentrations to identify an equilibrium in which all included loci may be amplified. Once the method and materials of this invention are disclosed, various methods of selecting loci, primer pairs, and amplification techniques for use in the method and kit of this invention are likely to be suggested to one skilled in the art. All such methods are intended to be within the scope of the appended claims.

Of particular importance in the practice of the method of this invention is the size range of amplified alleles produced from the individual loci which are co-amplified in the multiplex amplification reaction step. For ease of analysis with current technologies, systems which can be detected by amplification of fragments smaller than 500 bases are most preferable.

Practice of the method of the present invention begins with selection of a set of loci comprising at least thirteen STR loci, which can be co-amplified in a single multiplex amplification reaction. Selection of loci and oligonucleotide primers used to amplify the loci in the multiplex amplification reaction of the present method is described herein below, and illustrated in the Examples below.

C. Use of Multiplexes of Three Loci to Develop Multiplexes Using More than Three Loci Any one of a number of different techniques can be used to select a set of loci for use in the present invention. One preferred technique for developing useful sets of loci for use in this method of analysis is described below. Once a multiplex containing three STR loci is developed, it may be used as a core to create multiplexes containing more than three loci. New combinations of more than three loci can, thus, be created which include the first three loci. For example, the core multiplex containing loci D7S820, D13S317, and D5S818 was used to generate derivative multiplexes of:

D16S539, D7S820, D13S317, and D5S818;

HUMCSF1PO, HUMTPOX, D16S539, D7S820, D13S317, and D5S818;

HUMCSF1PO, HUMTPOX, HUMTH01, D16S539, D7S820, D13S317, and D5S818;

HUMCSF1PO, HUMTPOX, HUMTH01, HUMvWFA31, D16S539, D7S820, D13S317, and D5S818;

D3S1358, D5S818, D7S820, D8S1179, D13S317, D16S539, D18S51, D21S11, HUMCSF1PO, HUMFIBRA, HUMTH01, HUMTPOX, and HUMvWA31;

S159, HUMCSF1P0, D16S539, D7S820, D13S317, and D5S818; D3S1358, D5S818, D7S820, D8S1179, D13S317, D16S539, D18S51, D21S11, HUMCSF1PO, HUMFIBRA, HUMTH01, HUMTPOX, and HUMvWFA31; and D3S1358, D5S818, D7S820, D8S1179, D13S317, D16S539, D18S51, D21S11, HUMCSF1PO, HUMFIBRA, HUMTH01, HUMTPOX, HUMvWFA31, G475, S159, and Amelogenin.

It is contemplated that core sets of loci can be used to generate other appropriate derivative sets of STR loci for multiplex analysis using the method of this invention. Regardless of what method is used to select the loci analyzed using the method of the present invention, all the loci selected for multiplex analysis share the following characteristics: (1) they produce sufficient amplification product to allow evaluation; (2) they generate few if any artifacts due to the addition (or lack of addition) of a base to the amplified alleles during the multiplex amplification step; (3) they generate few, if any, artifacts due to premature termination of amplification reactions by a polymerase; and (4) they produce little or no "trailing" bands of smaller molecular weight from consecutive single base deletions below a given authentic amplified allele. See, e.g., Schumm et al., *Fourth International Symposium on Human Identification* 1993, pp. 177–187 (pub. by Promega Corp., 1994).

The same technique used to identify the set of at least three loci, described above, can be applied to select thirteen or more loci of human genomic DNA or multiplex analysis, according to a preferred embodiment of the method of analysis of the present invention. Any set of loci identified as described above is suitable for multiplex analysis in accordance with the present invention, provided the set of loci comprises at least thirteen STR loci. More preferably, at least four of the at least thirteen STR loci analyzed according to the present invention are selected from the group of loci consisting of:

D3S1539, D4S2368, D5S818, D7S820, D9S930, D10S1239, D13S317, D14S118, D14S548, D14S562, D16S490, D16S539, D16S753, D17S1298, D17S1299, D19S253, D20S481, D22S683, HUMCSF1PO, HUMTPOX, HUMTH01, HUMF13AO1, HUMBFXIII, HUMLIPOL, and HUMvWFA31.

Even more preferably, the set of loci analyzed according to the present invention includes all thirteen CODIS loci, i.e. D3S1358, D5S818, D7S820, D8S1179, D13S317, D16S539, D18S51, D21S11, HUMCSF1PO, HUMFIBRA, HUMTH01, HUMTPOX, and HUMvWFA31.

At least one of the loci selected for co-amplification in the present multiplex reaction is preferably an STR locus with a repeat unit of five to seven bases or base pairs in length, more preferably an STR locus with a pentanucleotide repeat. As is demonstrated in U.S. patent application Ser. No. 09/018,584, which is incorporated by reference herein, loci with such intermediate length repeats can be amplified with minimal incidence of artifacts, e.g. due to repeat slippage. Three such loci with pentanucleotide repeats, G475, C221 and S159, are included in the sets of loci identified immediately above. The terms "G475", "C221", and "S159", as used herein, refer to names assigned to pentanucleotide repeat loci identified, as described in U.S. patent application Ser. No. 09/018,584, incorporated by reference above. Each name corresponds to a clone from which each pentanucleotide locus was identified. The sequence of the G475 clone, described therein as SEQ ID NO:34, is identified herein as SEQ ID NO:108. The sequence of the C221 clone, described therein as SEQ ID NO:2, is identified herein as SEQ ID NO:109. The sequence of the S159 clone, described therein as SEQ ID NO: 26, is identified herein as SEQ ID NO:110.

Individual primers and primer pairs identified for use in amplifying G475, C221, and S159 therein can also be used to amplify the same loci in the sets of at least thirteen loci co-amplified and analyzed according to the present invention.

The set of loci selected for co-amplification and analysis according to the invention preferably further comprises at least one locus in addition to the at least thirteen STR loci. The additional locus preferably includes a sequence polymorphism, or another feature which identifies a particular characteristic which separates the DNA of an individual from the DNA of other individuals in the population. The additional locus more preferably is a locus which identifies the gender of the source of the DNA sample analyzed. When the DNA sample is human genomic DNA, a gender identifying locus such as the Amelogenin locus is preferably selected for co-amplification and analysis according to the present method. The Amelogenin locus is identified by GenBank as HUMAMELY (when used to identify a locus on the Y chromosome contained in male DNA) or as HUMAMELX (when used to identify a locus on the X chromosome in male or female DNA). When the Amelogenin locus is co-amplified in the same multiplex amplification reaction as the set of at least thirteen short tandem repeat loci, the sequence of at least one of the primers used to amplify this particular locus in the multiplex amplification reaction preferably has a sequence selected from: SEQ ID NO:86, SEQ ID NO:105, and SEQ ID NO:87.

D. Selection of Primers

Once a set of loci for co-amplification in a single multiplex reaction is identified, one can determine primers suitable for co-amplifying each locus in the set. Care should be used in selecting the sequence of primers used in the multiplex reaction. Inappropriate selection of primers can produce several undesirable effects such as lack of amplification, amplification at multiple sites, primer dimer formation, undesirable interaction of primer sequences from different loci, production of alleles from one locus which overlap with alleles from another, or the need for amplification conditions or protocols for the different loci which are incompatible in a multiplex. Primers used in the present method or included in the present kits of the invention are preferably selected according to the following selection process.

Primers are preferably developed and selected for use in the multiplex systems of the invention by employing a re-iterative process of selecting primer sequences, mixing the primers for co-amplification of the selected loci, co-amplifying the loci, then separating and detecting the amplified products. Initially, this process often produces the amplified alleles in an imbalanced fashion (i.e., higher product yield for some loci than for others) and may also generate amplification products which do not represent the alleles themselves. These extra fragments may result from any number of causes described above.

To eliminate such extra fragments from the multiplex systems, individual primers from the total set are used with primers from the same or other loci to identify which primers contribute to the amplification of the extra fragments. Once two primers which generate one or more of the fragments are identified, one or both contributors are modified and retested, either in a pair alone or in the multiplex system (or a subset of the multiplex system). This process is repeated until evaluation of the products yields amplified alleles with no or an acceptable level of extra fragments in the multiplex system.

On occasion, extra fragments can be eliminated by labeling the opposite primer in a primer pair. This change reveals the products of the opposing primer in the detection step. This newly labeled primer may amplify the true alleles with greater fidelity than the previously labeled primer generating the true alleles as a greater proportion of the total amplification product.

The determination of primer concentration may be performed either before or after selection of the final primer sequences, but is preferably performed after that selection. Generally, increasing primer concentration for any particular locus increases the amount of product generated for that locus. However, this is also a re-iterative process because increasing yield for one locus may decrease it for one or more other loci. Furthermore, primers may interact directly affecting yield of the other loci. Linear increases in primer concentration do not necessarily produce linear increases in product yield for the corresponding locus.

Locus to locus balance is also affected by a number of parameters of the amplification protocol such as the amount of template used, the number of cycles of amplification, the annealing temperature of the thermal cycling protocol, and the inclusion or exclusion of an extra extension step at the end of the cycling process. Absolutely even balance across all alleles and loci is generally not achieved.

The process of multiplex system development may also be a re-iterative process in another sense described, above. That is, it is possible, first, to develop a multiplex system for a small number of loci, this system being free or nearly free of extra fragments from amplification. Primers of this system may be combined with primers for one or more additional loci. This expanded primer combination may or may not produce extra fragments from amplification. In turn, new primers may be introduced and evaluated.

One or more of the re-iterative selection processes described above are repeated until a complete set of primers is identified which can be used to co-amplify the at least thirteen loci selected for co-amplification as described above. It is understood that many different sets of primers may be developed to amplify a particular set of loci.

Synthesis of the primers used in the present method can be conducted using any standard procedure for oligonucleotide synthesis known to those skilled in the art. At least one primer for each locus is preferably covalently attached to a dye label, as described in Section F, below.

Table 1, below, provides a list sequences of primers which have been determined to be suitable for use in amplifying the corresponding polymorphic STR loci listed therein. At least one primer listed in Table 1 is preferably used to amplify at least one of the loci selected for co-amplification and analysis as described above. It is understood that other primers could be identified which are suitable for simultaneous amplification of the loci listed below.

TABLE 1

| Locus | Primer SEQ ID NO:'s |
|---|---|
| D7S820 | 1, 2, 80 and 81 |
| D13S317 | 3, 4, 82 and 83 |
| D5S818 | 5, 6, 84 and 85 |
| D3S1539 | 7, 8 and 49 |
| D17S1298 | 9 and 10 |
| D20S481 | 11, 12, 52 and 53 |
| D9S930 | 13, 14, 55 and 61 |
| D10S1239 | 15, 16 and 54 |
| D14S118 | 17 and 18 |
| D14S562 | 19 and 20 |

TABLE 1-continued

| Locus | Primer SEQ ID NO:'s |
|---|---|
| D14S548 | 21 and 22 |
| D16S490 | 23 and 24 |
| D16S753 | 25 and 26 |
| D17S1299 | 27 and 28 |
| D16S539 | 29, 30, 58, 79 and 97 |
| D22S683 | 31 and 32 |
| HUMCSF1PO | 33, 34, 77, 78 and 98 |
| HUMTPOX | 35, 36, 72 and 73 |
| HUMTH01 | 37, 38, 66, 67 and 103 |
| HUMvWFA31 | 39, 40, 59, 60 and 76 |
| HUMF13A01 | 41 and 42 |
| HUMFESFPS | 43 and 44 |
| HUMBFXIII | 45 and 46 |
| HUMLIPOL | 47 and 48 |
| D19S253 | 50 and 51 |
| D4S2368 | 56 and 57 |
| D18S51 | 62, 63, 101 and 102 |
| D21S11 | 64 and 65 |
| D3S1358 | 68, 69 and 106 |
| HUMFIBRA | 70, 71 and 107 |
| D8S1179 | 74, 75 and 104 |
| G475 | 88, 89 and 94 |
| S159 | 90, 91, 92, 93, 95 and 96 |
| C221 | 99 and 100 |

E. Preparation of DNA Samples

Samples of genomic DNA can be prepared for use in the method of this invention using any method of DNA preparation which is compatible with the amplification of DNA. Many such methods are known by those skilled in the art. Examples include, but are not limited to DNA purification by phenol extraction (Sambrook, J., et al. (1989) *Molecular Cloning: A Laboratory Manual, Second Edition*, Cold Spring Harbor Laboratory Press, Cold Spring Harbor, N.Y., pp. 9.14–9.19), and partial purification by salt precipitation (Miller, S. et al. (1988) *Nucl. Acids Res.* 16:1215) or chelex (Walsh et al., (1991) *BioTechniques* 10:506–513, Comey, et al., (1994) *Forensic Sci.* 39:1254) and the release of unpurified material using untreated blood (Burckhardt, J. (1994) *PCR Methods and Applications* 3:239–243, McCabe, Edward R. B.,(1991) *PCR Methods and Applications* 1:99–106, Nordvåg, Bjørn-Yngvar (1992) *BioTechniques* 12:4 pp. 490–492).

When the at least one DNA sample to be analyzed using the method of this invention is human genomic DNA, the DNA is preferably prepared from tissue, selected from the group consisting of blood, semen, vaginal cells, hair, saliva, urine, bone, buccal samples, amniotic fluid containing placental cells or fetal cells, chorionic villus, and mixtures of any of the tissues listed above.

Optionally, DNA concentrations can be measured prior to use in the method of the present invention, using any standard method of DNA quantification known to those skilled in the art. In such cases, the DNA concentration is preferably determined by spectrophotometric measurement as described by Sambrook, J., et al. (1989), supra, Appendix E.5, or fluorometrically using a measurement technique such as that described by Brunk C. F., et al. (1979), *Anal Biochem* 92: 497–500. The DNA concentration is more preferably measured by comparison of the amount of hybridization of DNA standards with a human-specific probe such as that described by Waye, J. S., et al. (1991) "Sensitive and specific quantification of human genomic deoxyribonucleic acid (DNA) in forensic science specimens: casework examples," *J. Forensic Sci.*, 36:1198–1203. Use of too much template DNA in the amplification reactions can produce artifacts which appear as extra bands which do not represent true alleles.

F. Amplification of DNA

Once a sample of genomic DNA is prepared, the targeted loci can be co-amplified in the multiplex amplification step of the present method. Any one of a number of different amplification methods can be used to amplify the loci, including, but not limited to, polymerase chain reaction (PCR) (Saiki, R. K., et al. (1985), *Science* 230: 1350–1354), transcription based amplification (Kwoh, D. Y., and Kwoh, T. J. (1990), *American Biotechnology Laboratory*, October, 1990) and strand displacement amplification (SDA) (Walker, G. T., et al. (1992) *Proc. Natl. Acad. Sci., U.S.A.* 89: 392–396). Preferably, the DNA sample is subjected to PCR amplification using primer pairs specific to each locus in the set. Reference is made to the Sequence Listing at the end of this specification for details of the primer sequences used in the Examples below, some of which sequences are alternative embodiments of this invention.

At least one primer for each locus is preferably covalently attached to a dye label, more preferably a fluorescent dye label. The primers and dyes attached thereto are preferably selected for the multiplex amplification reaction, such that alleles amplified using primers for each locus labeled with one color do not overlap the alleles of the other loci in the set co-amplified therein using primers labeled with the same color, when the alleles are separated, preferably, by gel or capillary electrophoresis.

In a particularly preferred embodiment of the method of the present invention, at least one primer for each locus co-amplified in the multiplex reaction is labeled with a fluorescent label prior to use in the reaction. Fluorescent labels suitable for attachment to primers for use in the present invention are commercially available. See, e.g. fluorescein and carboxy-tetramethylrhodamine labels and their chemical derivatives from PE Biosystems and Molecular Probes. Most preferably, at least three different labels are used to label the different primers used in the multiplex amplification reaction. When a size marker is included to evaluate the multiplex reaction, the primers used to prepare the size marker are preferably labeled with a different label from the primers used to amplify the loci of interest in the reaction.

Details of the most preferred amplification protocol for each of the most preferred combinations of loci for use in the method of this invention are given in the Examples below. Reference is also made to the Examples for additional details of the specific procedure relating to each multiplex. The sequences of the locus-specific primers used in the Examples include a number of nucleotides which, under the conditions used in the hybridization, are sufficient to hybridize with an allele of the locus to be amplified and to be essentially free from amplification of alleles of other loci. Reference is made to U.S. Pat. No. 5,192,659 to Simons, the teaching of which is incorporated herein by reference for a more detailed description of locus-specific primers.

G. Separation and Detection of DNA Fragments

Once a set of amplified alleles is produced from the multiplex amplification step of the present method, the amplified alleles are evaluated. The evaluation step of this method can be accomplished by any one of a number of different means, the most preferred of which are described below.

Electrophoresis is preferably used to separate the products of the multiplex amplification reaction, more preferably capillary electrophoresis (see, e.g., Buel, Eric et al. (1998), *Journal of Forensic Sciences;* 43:(1) pp. 164–170) or denaturing polyacrylamide gel electrophoresis (see, e.g., Sambrook, J. et al. (1989) In *Molecular Cloning—A Laboratory Manual,* 2nd edition, Cold Spring Harbor Laboratory Press, pp. 13.45–1 3.57). Gel preparation and electrophoresis procedures and conditions for suitable for use in the evaluating step of the method of this invention are illustrated in the Examples, below. Separation of DNA fragments in a denaturing polyacrylamide gel and in capillary electrophoresis occurs based primarily on fragment size.

Once the amplified alleles are separated, the alleles and any other DNA in the gel or capillary (e.g., DNA size markers or an allelic ladder) can then be visualized and analyzed. Visualization of the DNA in the gel can be accomplished using any one of a number of prior art techniques, including silver staining or reporters such as radioisotopes, fluorescers, chemiluminescers and enzymes in combination with detectable substrates. However, the preferred method for detection of multiplexes containing thirteen or more loci is fluorescence (see, e.g., Schumm, J. W. et al. in *Proceedings from the Eighth International Symposium on Human Identification,* (pub. 1998 by Promega Corporation), pp. 78–84; Buel, Eric et al. (1998), supra.), wherein primers for each locus in the multiplexing reaction is followed by detection of the labeled products employing a fluorometric detector. The references cited above, which describe prior art methods of visualizing alleles, are incorporated by reference herein.

The alleles present in the DNA sample are preferably determined by comparison to a size standard such as a DNA marker or a locus-specific allelic ladder to determine the alleles present at each locus within the sample. The most preferred size marker for evaluation of a multiplex amplification containing two or more polymorphic STR loci consists of a combination of allelic ladders for each of the loci being evaluated. See, e.g., Puers, Christoph et al., (1993) *Am J. Hum Genet.* 53:953–958, Puers, Christoph, et al. (1994) *Genomics* 23:260–264. See also, U.S. Pat. No's 5,599,666; 5,674,686; and 5,783,406 for descriptions of allelic ladders suitable for use in the detection of STR loci, and methods of ladder construction disclosed therein.

Following the construction of allelic ladders for individual loci, these may be mixed and loaded for gel electrophoresis at the same time as the loading of amplified samples occurs. Each allelic ladder co-migrates with alleles in the sample from the corresponding locus.

The products of the multiplex reactions of the present invention can be evaluated using an internal lane standard, a specialized type of size marker configured to run in the same lane of a polyacrylamide gel or same capillary. The internal lane standard preferably consists of a series of fragments of known length. The internal lane standard more preferably is labeled with a fluorescent dye which is distinguishable from other dyes in the amplification reaction.

Following construction of the internal lane standard, this standard can also be mixed with amplified sample or allelic ladders and loaded for electrophoresis for comparison of migration in different lanes of gel electrophoresis or different capillaries of capillary electrophoresis. Variation in the migration of the internal lane standard indicates variation in the performance of the separation medium. Quantitation of this difference and correlation with the allelic ladders allows correction in the size determination of alleles in unknown samples.

H. Preferred Detection Technique: Fluorescent Detection

In one of the most preferred embodiments of the method of this invention, fluorescent detection is used to evaluate the amplified alleles in the mixture produced by the multiplex amplification reaction. Below is a brief summary of how that method of detection preferably is practiced.

With the advent of automated fluorescent imaging, faster detection and analysis of multiplex amplification products can be achieved. For fluorescent analysis, one fluorescent labeled primer can be included in the amplification of each locus. Fluorescent labeled primers preferably suited for use in the present invention include the fluorescein-labeled (FL-), carboxy-tetramethylrhodamine-labeled (TMR-), and 5,6-carboxyrhodamine 6G-labeled (R6G) primers, such as are illustrated in the Examples, below. Separation of the amplified fragments produced using such labeled primers is achieved preferably by slab gel electrophoresis or capillary electrophoresis. The resulting separated fragments can be analyzed using fluorescence detection equipment such as an ABI PRISM® 310 Genetic Analyzer, an ABI PRISM® 377 DNA Sequencer (Applied Biosystems Division, Perkin Elmer, Foster City, Calif.), or a Hitachi FMBIO® II Fluorescent Scanner (Hitachi Software Engineering America, Ltd. South San Francisco, Calif.).

In summary, the method of this invention is most preferably practiced using fluorescent detection as the detection step. In this preferred method of detection, one or both of each pair of primers used in the multiplex amplification reaction has a fluorescent label attached thereto, and as a result, the amplified alleles produced from the amplification reaction are fluorescently labeled. In this most preferred embodiment of the invention, the amplified alleles are subsequently separated by capillary electrophoresis and the separated alleles visualized and analyzed using a fluorescent image analyzer.

Fluorescent detection is preferred over radioactive methods of labeling and detection, because it does not require the use of radioactive materials, and all the regulatory and safety problems which accompany the use of such materials.

Fluorescent detection employing labeled primers is also preferred over other non-radioactive methods of detection, such as silver staining, because fluorescent methods of detection generally reveal fewer amplification artifacts than silver staining. The smaller number of artifacts are due, in part, to the fact that only amplified strands of DNA with labels attached are detected in fluorescent detection, while both strands of every amplified allele of DNA produced from the multiplex amplification reaction is stained and detected using the silver staining method of detection.

I. Kit

The present invention is also directed to kits that utilize the process described above. A basic kit comprises a container having one or more locus-specific primers. Instructions for use optionally may be included.

Other optional kit components may include an allelic ladder directed to each of the specified loci, a sufficient quantity of enzyme for amplification, amplification buffer to facilitate the amplification, loading solution for preparation of the amplified material for electrophoresis, genomic DNA as a template control, a size marker to insure that materials migrate as anticipated in the separation medium, and a protocol and manual to educate the user and to limit error in use. The amounts of the various reagents in the kits also can be varied depending upon a number of factors, such as the optimum sensitivity of the process. It is within the scope of this invention to provide test kits for use in manual applications or test kits for use with automated detectors or analyzers.

EXAMPLES

The following Examples are presented to illustrate the advantages of the present invention and to assist one of ordinary skill in making and using the same. The Examples are intended to be illustrative, and are not intended in any way to otherwise limit the scope of the claims or protection granted by the patent.

The human genomic DNA samples assayed in the Example below were prepared from blood or tissue culture cells, using a standard procedure described by Miller and Dykes in (Miller, S. et al. (1988) Nucl. Acids Res. 16:1215). The isolation and quantification methods described therein are generally known to those skilled in the art and are preferred, but not required, for application of the invention.

Each Example below is an example of the use of the method of this invention, to determine simultaneously the alleles present in at least thirteen loci from one or more DNA samples of human genomic DNA. Each set of loci co-amplified below includes the thirteen short tandem repeat loci identified for use in the CODIS system (i.e., D3S1358, HUMTHO1, D21S11, D18S51, HUMvWFA31, D8S1179, HUMTPOX, HUMFIBRA, D5S818, D13S317, D7S820, D16S539, and HUMCSF1PO). Some sets of loci co-amplified below also include one or more additional short tandem repeat loci, such as loci with pentanucleotide repeats (e.g., G475, S159, or C221), and a non-STR locus, Amelogenin.

Table 2 summarizes which set of loci was co-amplified in the multiplex amplification reaction described in each Example below. The table also indicates which primer pair was used to amplify each such locus in each such multiplex reaction. One primer of each primer pair listed on Table 2 was fluorescently labeled prior to being used in the multiplex amplification reaction. In some cases, a different label was used to label primers to different loci, such that the alleles produced using the different primers could be distinguished from one another when detected with a laser-activated fluorescence detection device.

Three different fluorescent labels were used in the Examples below, described as "FL" to indicate fluorescein-labeled, "TMR" to indicate carboxy-tetramethylrhodamine-labeled, and "R6G" to indicate 5,6-carboxyrhodamine 6G in Table 2, below. Table 2 also indicates which primer of each pair of primers used in the multiplex amplification reaction was so labeled in each Example (e.g., "FL-69" means the primer with SEQ ID NO:69 was labeled at its 5' end with fluorescein prior to being used in the multiplex amplification reaction). In the text of each of the Examples, however, the label abbreviation is placed immediately before the SEQ ID NO of the labeled primer used in the amplification reaction described therein (e.g., "FL-SEQ ID NO:2" instead of "FL-2").

TABLE 2

| Example | Loci Amplified | Primer Pair: SEQ ID NO's Used | Fluorescent Label(s) Used |
|---|---|---|---|
| 1 | D3S1358 | 68, 69 | FL-69 |
|  | HUMTHO1 | 66, 67 | FL-66 |
|  | D21S11 | 64, 65 | FL-65 |
|  | D18S51 | 62, 63 | FL-62 |
|  | HUMvWFA31 | 76, 40 | TMR-40 |
|  | D8S1179 | 74, 75 | TMR-75 |

TABLE 2-continued

| Example | Loci Amplified | Primer Pair: SEQ ID NO's Used | Fluorescent Label(s) Used |
|---|---|---|---|
|  | HUMTPOX | 72, 73 | TMR-73 |
|  | HUMFIBRA | 70, 71 | TMR-70 |
|  | D5S818 | 84, 85 | R6G-85 |
|  | D13S317 | 82, 83 | R6G-83 |
|  | D7S820 | 80, 81 | R6G-80 |
|  | D16S539 | 29, 79 | R6G-79 |
|  | HUMCSF1PO | 77, 78 | R6G-78 |
| 2, 3 | D3S1358 | 68, 69 | FL-69 |
|  | HUMTHO1 | 66, 67 | FL-66 |
|  | D21S11 | 64, 65 | FL-65 |
|  | D18S51 | 62, 63 | FL-62 |
|  | G475 | 88, 89 | FL-88 |
|  | Amelogenin | 86, 87 | TMR-86 |
|  | HUMvWFA31 | 76, 40 | TMR-40 |
|  | D8S1179 | 74, 75 | TMR-75 |
|  | HUMTPOX | 72, 73 | TMR-73 |
|  | HUMFIBRA | 70, 71 | TMR-70 |
|  | D5S818 | 84, 85 | R6G-85 |
|  | D13S317 | 82, 83 | R6G-83 |
|  | D7S820 | 80, 81 | R6G-80 |
|  | D16S539 | 29, 79 | R6G-79 |
|  | HUMCSF1PO | 77, 78 | R6G-78 |
|  | S159 | 90, 91 | R6G-91 |
| 4 | D3S1358 | 68, 69 | FL-69 |
|  | HUMTHO1 | 66, 67 | FL-66 |
|  | D21S11 | 64, 65 | FL-65 |
|  | D18S51 | 62, 63 | FL-62 |
|  | G475 | 88, 89 | FL-88 |
|  | Amelogenin | 86, 87 | TMR-86 |
|  | HUMvWFA31 | 76, 40 | TMR-40 |
|  | D8S1179 | 74, 75 | TMR-75 |
|  | HUMTPOX | 72, 73 | TMR-73 |
|  | HUMFIBRA | 70, 71 | TMR-70 |
|  | D5S818 | 84, 85 | FL-85 |
|  | D13S317 | 82, 83 | FL-83 |
|  | D7S820 | 80, 81 | FL-80 |
|  | D16S539 | 29, 79 | FL-79 |
|  | HUMCSF1PO | 77, 78 | FL-78 |
|  | S159 | 90, 91 | FL-91 |
| 5 | D3S1358 | 68, 69 | FL-69 |
|  | HUMTHO1 | 66, 67 | FL-66 |
|  | D21S11 | 64, 65 | FL-65 |
|  | D18S51 | 62, 63 | FL-62 |
|  | G475 | 88, 94 | FL-94 |
|  | Amelogenin | 86, 87 | TMR-86 |
|  | HUMvWFA31 | 76, 40 | TMR-40 |
|  | D8S1179 | 74, 75 | TMR-75 |
|  | HUMTPOX | 72, 73 | TMR-73 |
|  | HUMFIBRA | 70, 71 | TMR-70 |
|  | D5S818 | 84, 85 | FL-85 |
|  | D13S317 | 82, 83 | FL-83 |
|  | D7S820 | 80, 81 | FL-80 |
|  | D16S539 | 29, 79 | FL-79 |
|  | HUMCSF1PO | 77, 78 | FL-78 |
|  | S159 | 95, 96 | FL-96 |
| 6 | D3S1358 | 69, 106 | FL-69 |
|  | HUMTHO1 | 38, 103 | FL-38 |
|  | D21S11 | 64, 65 | FL-65 |
|  | D18S51 | 101, 102 | FL-101 |
|  | S159 | 92, 93 | FL-93 |
|  | Amelogenin | 105, 87 | TMR-105 |
|  | HUMvWFA31 | 76, 40 | TMR-40 |
|  | D8S1179 | 104, 75 | TMR-104 |
|  | HUMTPOX | 72, 73 | TMR-72 |
|  | HUMFIBRA | 70, 107 | TMR-70 |
|  | D5S818 | 84, 85 | FL-85 |
|  | D13S317 | 3, 4 | FL-4 |
|  | D7S820 | 80, 81 | FL-80 |
|  | D16S539 | 29, 97 | FL-29 |
|  | HUMCSF1PO | 77, 98 | FL-98 |
|  | C221 | 99, 100 | FL-99 |

Example 1

Fluorescent Detection of Multiplex Amplification of Loci D3S1358, HUMTH01, D21S11, D18S51, HUMvWFA31, D8S1179, HUMTPOX, HUMFIBRA, D5S818, D7S820, D13S317, D16S539, and HUMCSF1PO as detected with the ABI PRISM® 310 Genetic Analyzer In this Example, a DNA template was amplified simultaneously at the individual loci D3S1358, HUMTH01, D21S11, D18S51, HUMvWFA31, D8S1179, HUMTPOX, HUMFIBRA, D5S818, D7S820, D13S317, D16S539, and HUMCSF1PO in a single reaction vessel. The PCR amplification was performed in 25 μl of 1× Gold ST*R Buffer (50 mM KCl, 10 mM Tris-HCl (pH 8.3 at 25° C.), 0.1% Triton X-100, 1.5 mM MgCl$_2$, 160 μg/ml BSA and 200 μM each of dATP, dCTP, dGTP and dTTP) using 1 ng template, and 3.25 U AmpliTaq Gold™ DNA Polymerase. A GeneAmp® PCR System 9600 (Perkin Elmer, Foster City, Calif.) was employed with the following amplification protocol: 96° C. for 12 min., then 10 cycles of 94° C. for 30 sec., ramp for 68 sec. to 58° C., hold for 30 sec., ramp 50 sec. to 70° C., hold for 45 sec., followed by 20 cycles of 90° C. for 30 sec., ramp 60 sec. to 58° C., hold for 30 sec., ramp for 50 sec, to 70° C., hold for 45 sec., followed by 1 cycle of 60° C. for 30 min.

Twenty-six amplification primers were used in combination, including 0.12 μM each D3S1358 primers 1 [SEQ ID NO:68] and 2 [FL-SEQ ID NO:69], 0.08 μM each HUMTH01 primers 1 [FL-SEQ ID NO:66] and 2 [SEQ ID NO:67], 0.3 μM each D21S11 primers 1 [SEQ ID NO:64] and 2 [FL-SEQ ID NO:65], 0.2 μM each D18S51 primers 1 [FL-SEQ ID NO:62] and 2 [SEQ ID NO:63], 1.1 μM each HUMvWFA31 primers 1 [SEQ ID NO:76] and 2 [TMR-SEQ ID NO:40], 1.8 μM each D8S1179 primers 1 [SEQ ID NO:74] and 2 [TMR-SEQ ID NO:75], 0.6 μM each HUMTPOX primers 1 [SEQ ID NO:72] and 2 [TMR-SEQ ID NO:73], 2.4 μM each HUMFIBRA primers 1 [TMR-SEQ ID NO:70] and 2 [SEQ ID NO:71], 0.2 μM each D5S818 primers 1 [SEQ ID NO:84] and 2 [R6G-SEQ ID NO:85], 0.1M each D13S317 primers 1 [SEQ ID NO:82] and 2 [R6G-SEQ ID NO:83], 0.2 μM each D7S820 primers 1 [R6G-SEQ ID NO:80] and 2 [SEQ ID NO:81], 0.15 μM each D16S539 primers 1 [SEQ ID NO:29] and 2 [R6G-SEQ ID NO:79], 0.2 μM each HUMCSF1PO primers 1 [SEQ ID NO:77] and 2 [R6G-SEQ ID NO:78].

Amplified products were separated using an ABI PRISM® 310 Genetic Analyzer. DNA samples were mixed with 24 μl of a loading solution (deionized formamide) and 1.0 μl of an internal lane size standard, denatured at 95° C. for 3 min., and chilled on ice prior to injection. Separation was carried out using Performance Optimized Polymer 4 (POP-4)(Perkin Elmer Biosystems, Foster City, Calif.) in a 47 cm×50 μm capillary. The manufacturer's GeneScan® run module GS STR POP4 (Id.) (1 ml) A was used. Conditions for the electrophoresis were a 5 second injection, injection kV was 15.0, run kV was 15.0, run temperature was 60° C., run time was 28 minutes and virtual filter A was used.

FIG. 1A is a printout of results of scanning the amplified fragments of each locus separated and detected with the ABI PRISM® 310 Genetic Analyzer, as described above. FIG. 1A shows amplification products of a DNA sample simultaneously co-amplified for the loci D3S1358, HUMTH01, D21S11, D18S51, HUMvWFA31, D8S1179, HUMTPOX, HUMFIBRA, D5S818, D7S820, D13S317, D16S539, and HUMCSF1PO. Peaks shown in Panel A are labeled with fluorescein, peaks shown in Panel B are labeled with carboxy-tetramethylrhodamine, and peaks shown in Panel C are labeled with 5,6 carboxyrhodamine 6G.

Figure 1B:
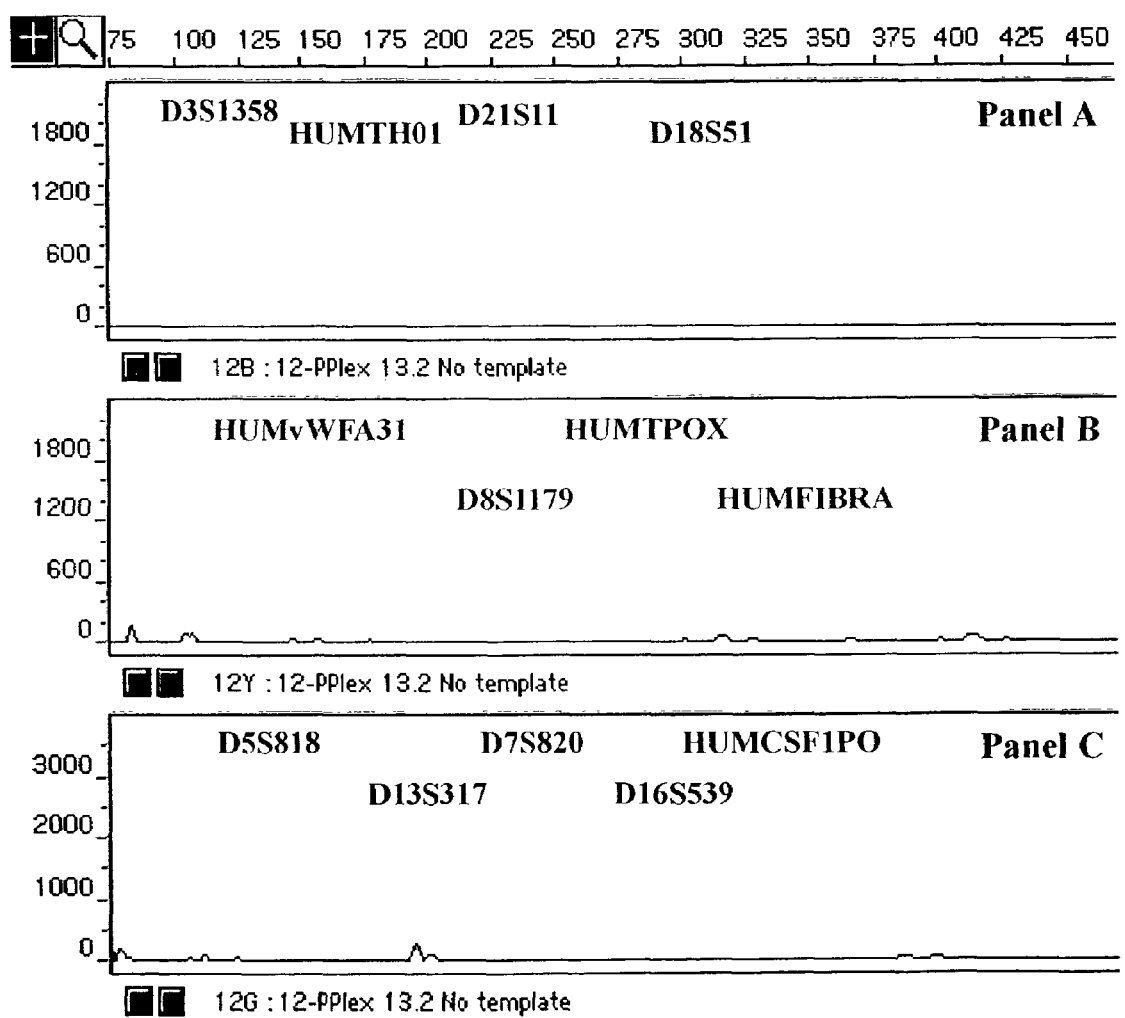
FIG. 1B is a plot of the output of three-color fluorescent detection of a control sample processed the same way as FIG. 1A, with no genomic DNA in the amplification reaction.

FIG. 1B is a printout of the results of scanning a sample prepared in the same way as the sample scanned in FIG. 1A, except that no DNA template was used in the amplification reaction. Peaks in this figure are background products resulting from dye conjugation and purification procedures and from undefined causes.

Example 2

Fluorescent Detection of Multiplex Amplification of Loci D3S1358, HUMTH01, D21S11, D18S51, G475, Amelogenin, HUMvWFA31, D8S1179, HUMTPOX, HUMFIBRA, D5S818, D7S820, D13S317, D16S539, HUMCSF1PO, and S159 as detected with the ABI PRISM® 310 Genetic Analyzer In this Example, a DNA template was amplified simultaneously at the individual loci D3S1358, HUMTH01, D21S11, D18S51, G475, Amelogenin, HUMvWFA31, D8S1179, HUMTPOX, HUMFIBRA, D5S818, D7S820, D13S317, D16S539, HUMCSF1PO and S159 in a single reaction vessel. The PCR amplification was performed in 25 μl of 1× Gold ST*R Buffer (50 mM KCl, 10 mM Tris-HCl (pH 8.3 at 25° C.), 0.1% Triton X-100, 1.5 mM MgCl$_2$, 160 μg/ml BSA and 200 μM each of dATP, dCTP, dGTP and dTTP) using 1 ng template, and 4 U AmpliTaq Gold™ DNA Polymerase. A GeneAmp® PCR System 9600 (Perkin Elmer, Foster City, Calif.) was employed with the following amplification protocol: 96° C. for 12 min., then 10 cycles of 94° C. for 30 sec., ramp for 68 sec. to 58° C., hold for 30 sec., ramp 50 sec. to 70° C., hold for 45 sec., followed by 20 cycles of 90° C. for 30 sec., ramp 60 sec. to 58° C., hold for 30 sec., ramp for 50 sec, to 70° C., hold for 45 sec., followed by 1 cycle of 60° C. for 30 min.

Thirty-two amplification primers were used in combination, including 0.12 μM each D3S1358 primers 1 [SEQ ID NO:68] and 2 [FL-SEQ ID NO:69], 0.08 μM each HUMTH01 primers 1 [FL-SEQ ID NO:66] and 2 [SEQ ID NO:67], 0.3%μM each D21 S11 primers 1 [SEQ ID NO:64] and 2 [FL-SEQ ID NO:65], 0.2 μM each D18S51 primers 1 [FL-SEQ ID NO:62] and 2 [SEQ ID NO:63], 0.24 μM each G475 primers 1 [FL-SEQ ID NO:88] and 2 [SEQ ID NO:89], 0.6 μM each Amelogenin primers 1 [TMR-SEQ ID NO:86] and 2 [SEQ ID NO:87], 1.1 μM each HUMvWFA31 primers 1 [SEQ ID NO:76] and 2 [TMR-SEQ ID NO:40], 1.8 μM each D8S1179 primers 1 [SEQ ID NO:74] and 2 [TMR-SEQ ID NO:75], 0.6 μM each HUMTPOX primers 1 [SEQ ID NO:72] and 2 [TMR-SEQ ID NO:73], 2.4 μM each HUMFIBRA primers 1 [TMR-SEQ ID NO:70] and 2 [SEQ ID NO:71], 0.2 μM each D5S818 primers 1 [SEQ ID NO:84] and 2 [R6G-SEQ ID NO:85], 0.1 μM each D13S317 primers 1 [SEQ ID NO:82] and 2 [R6G-SEQ ID NO:83], 0.2 μM each D7S820 primers 1 [R6G-SEQ ID NO:80] and 2 [SEQ ID NO:81], 0.15 μM each D16S539 primers 1 [SEQ ID NO:29] and 2 [R6G-SEQ ID NO:79], 0.2 μM each HUMCSF1PO primers 1 [SEQ ID NO:77] and 2 [R6G-SEQ ID NO:78] 0.1 μM each S159 primers 1 [SEQ ID NO:90] and 2 [R6G-SEQ ID NO:91]

Amplified products were separated using an ABI PRISM® 310 Genetic Analyzer. DNA samples were mixed with 24 μl of a loading solution (deionized formamide) and 1.0 μl of an internal lane size standard, denatured at 95° C. for 3 min., and chilled on ice prior to injection. Separation was carried out using Performance Optimized Polymer 4 (POP-4) (Perkin Elmer Biosystems, Foster City, Calif.) in a 47 cm×50 μm capillary. The manufacturer's GeneScan® run module GS STR POP4 (Id.)(1 ml) A was used. Conditions for the electrophoresis were a 5 second injection, injection kV was 15.0, run kV was 15.0, run temperature was 60° C., run time was 28 minutes and virtual filter A was used.

Figure 2A:
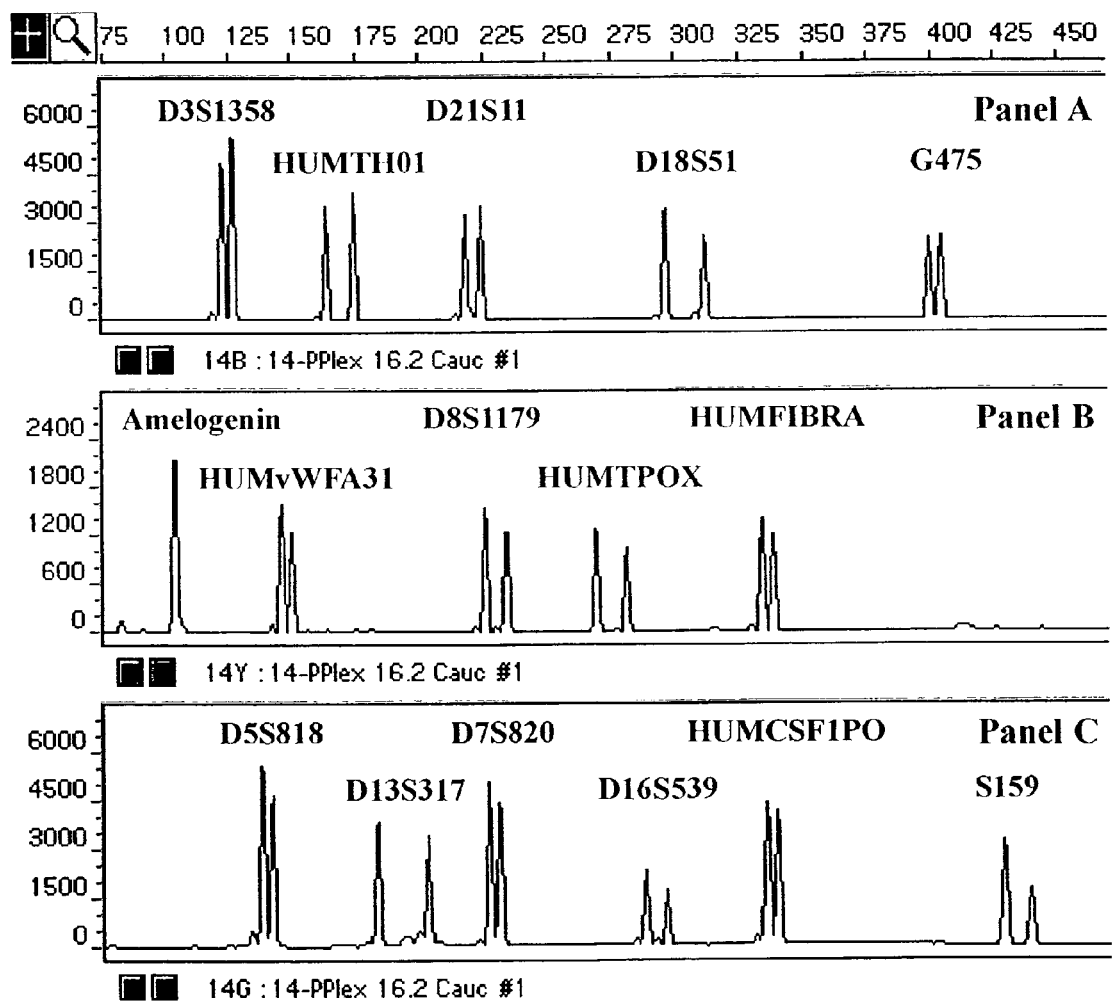
FIG. 2A is a plot of the output of three-color fluorescent detection of the products of simultaneous amplification of the loci D3S1358, D5S818, D7S820, D8S1179, D13S317, D16S539, D18S51, D21S11, HUMCSF1PO, HUMFIBRA, HUMTH01, HUMTPOX, HUMvWFA31, G475, S159, and Amelogenin of a sample of human genomic DNA, as detected with the ABI PRISM 310 Genetic Analyzer in Example 2.

FIG. 2A is a printout of results of scanning the amplified fragments of each locus separated and detected with the ABI PRISM® 310 Genetic Analyzer, as described above. FIG. 2A shows amplification products of a DNA sample simultaneously co-amplified for the loci D3S1358, HUMTH01, D21S11, D18S51, G475, Amelogenin, HUMvWFA31, D8S1179, HUMTPOX, HUMFIBRA, D5S818, D7S820, D13S317, D16S539, HUMCSF1PO, and S159. Peaks shown in Panel A are labeled with fluorescein, peaks shown in Panel B are labeled with carboxy-tetramethylrhodamine, and peaks shown in Panel C are labeled with 5,6 carboxyrhodamine 6G.

Figure 2B:
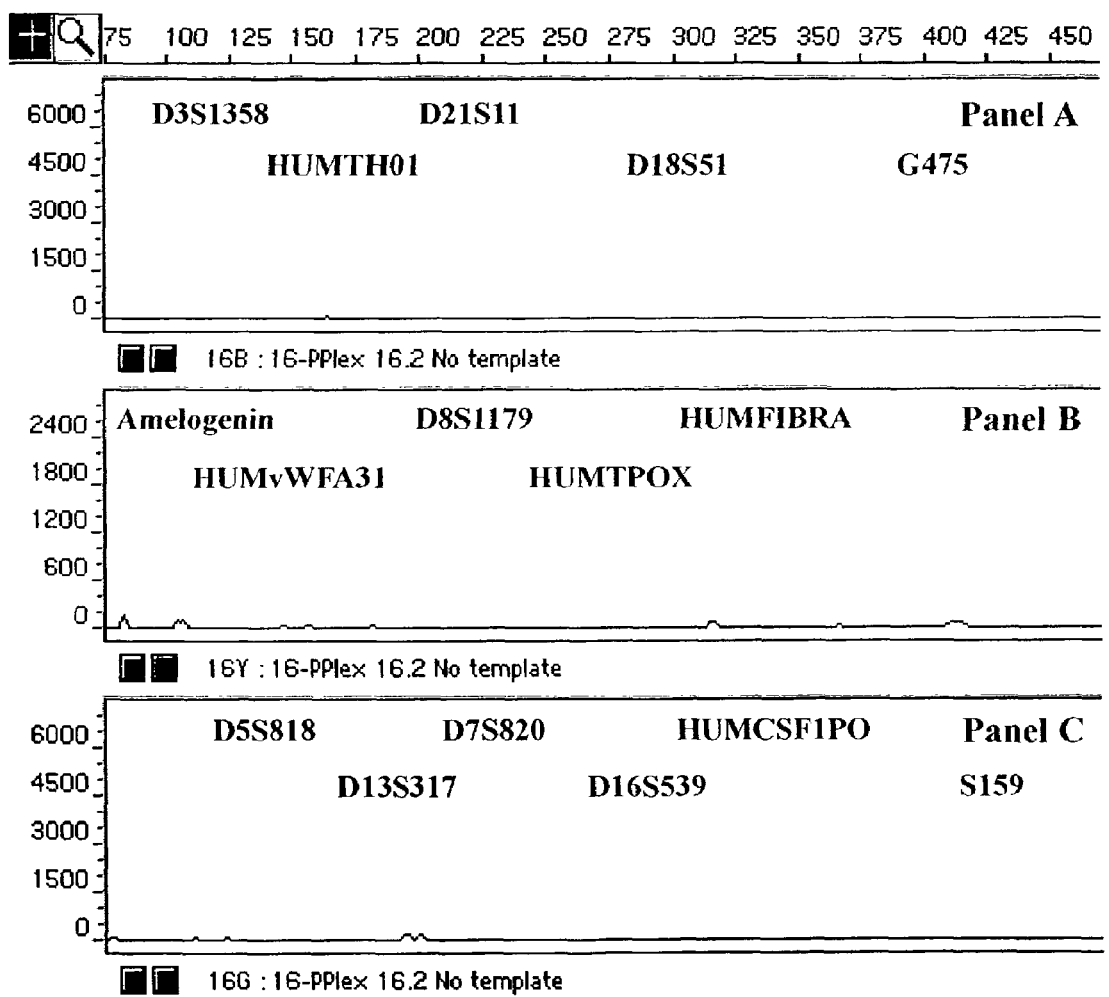
FIG. 2B is a plot of the output of three-color fluorescent detection of a control sample processed the same way as FIG. 2A, with no genomic DNA substrate in the amplification reaction.

FIG. 2B is a printout of the results of scanning a sample prepared in the same way as the sample scanned in FIG. 2A, except that no DNA template was used in the amplification reaction. Peaks in this figure are background products resulting from dye conjugation and purification procedures and from undefined causes.

Example 3

Fluorescent Detection of Multiplex Amplification of Loci D3S1358, HUMTH01, D21S11, D18S51, G475, Amelogenin, HUMvWFA31, D8S1179, HUMTPOX, HUMFIBRA, D5S818, D7S820, D13S317, D16S539, HUMCSF1PO, and S159 as detected with the ABI PRISM® 377 DNA Sequencer In this Example, a DNA template was amplified as in Example 2. Amplified products were separated using an ABI PRISM® 377 DNA Sequencer. This was carried out using a 0.2 mm thick, 5% Long Ranger™ Acrylamide (FMC Bio-Products, Rockland, Me.), 7M urea gel. DNA samples were mixed with 1.51 μl of a loading solution (88.25% formamide, 4.1 mM EDTA, 15 mg/ml Blue Dextran) and 0.5 μl of an internal lane size standard, denatured at 95° C. for 2 min., and chilled on ice prior to loading. Electrophoresis was carried out using the manufacturer's GeneScan® modules for Prerun (PR GS 36A-2400) and Run (GS 36A-2400). Run time was 3 hours and virtual filter A was used.

Figure 3A:
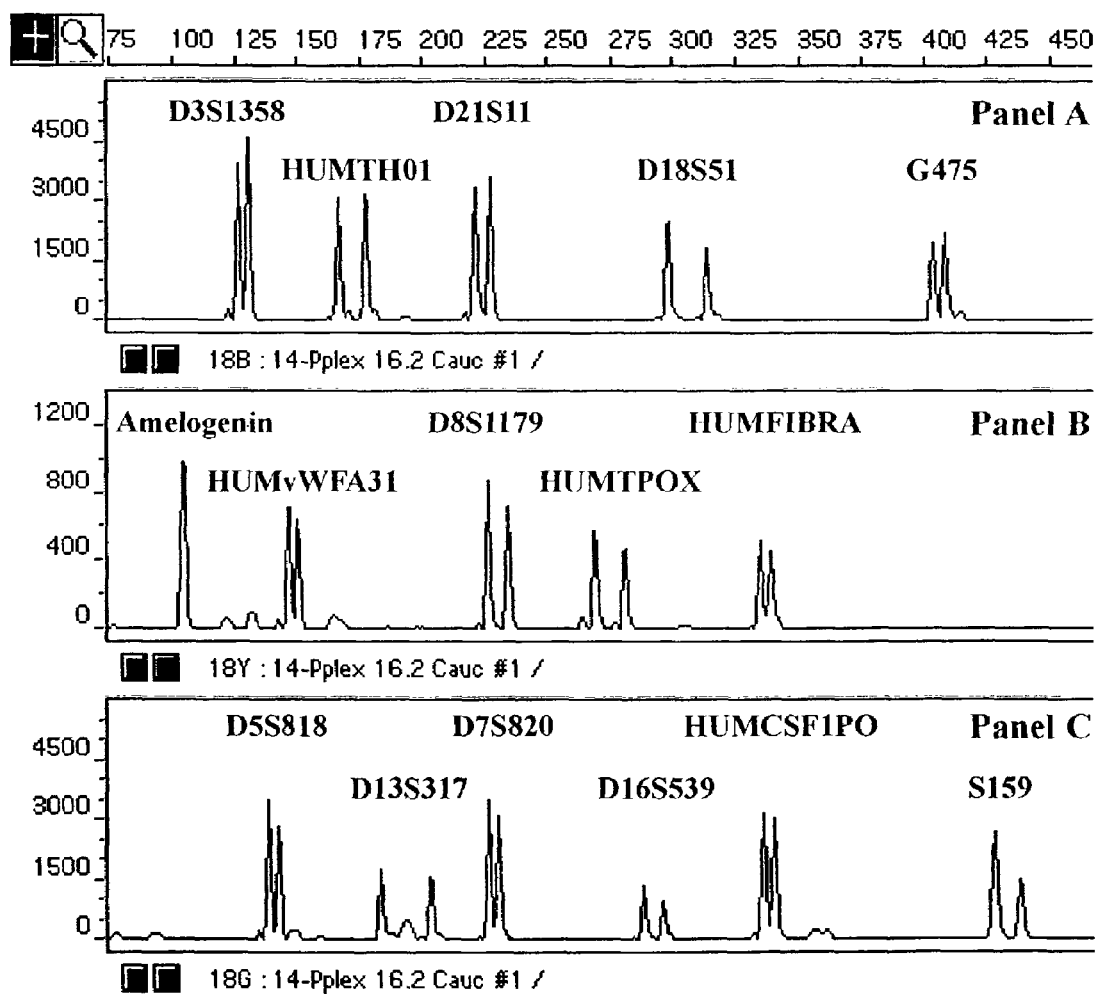
FIG. 3A is a plot of the output of three-color fluorescent detection of the products of simultaneous amplification of the loci D3S1358, D5S818, D7S820, D8S1179, D13S317, D16S539, D18S51, D21 S11, HUMCSF1PO, HUMFIBRA, HUMTH01, HUMTPOX, HUMvWFA31, G475, S159, and Amelogenin of a sample of human genomic DNA, as detected with an ABI PRISM® 377 DNA Sequencer in Example 3.

FIG. 3A is a printout of results of scanning the amplified fragments of each locus separated and detected with the ABI PRISM® 377 DNA Sequencer, as described above. FIG. 3A shows amplification products of a DNA sample simultaneously co-amplified for the loci D3S1358, HUMTH01, D21S11, D 18S51, G475, Amelogenin, HUMvWFA31, D8S1179, HUMTPOX, HUMFIBRA, D5S818, D7S820, D13S317, D16S539, HUMCSF1PO, and S159. Peaks shown in Panel A are labeled with fluorescein, peaks shown in Panel B are labeled with carboxy-tetramethylrhodamine, and peaks shown in Panel C are labeled with 5,6 carboxyrhodamine 6G.

Figure 3B:
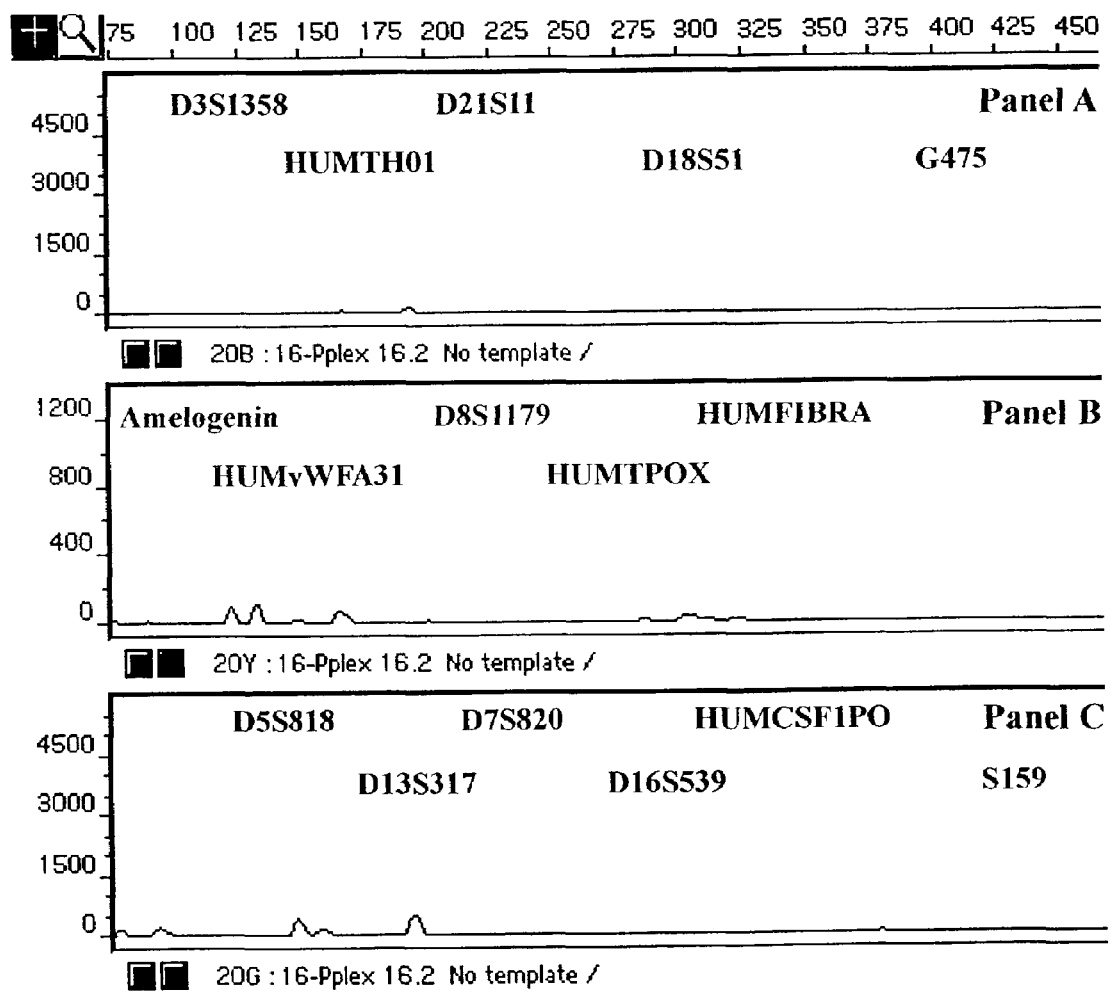
FIG. 3B is a plot of the output of three-color fluorescent detection of a control sample processed the same way as FIG. 3A, with no genomic DNA substrate in the amplification reaction.

FIG. 3B is a printout of the results of scanning a sample prepared in the same way as the sample scanned in FIG. 3A, except that no DNA template was used in the amplification reaction. Peaks in this figure are background products resulting from dye conjugation and purification procedures and from undefined causes.

Example 4

Fluorescent Detection of Multiplex Amplification of Loci D3S1358, HUMTH01, D21S11, D18S51, G475, Amelogenin, HUMvWFA31, D8S1179, HUMTPOX HUMFIBRA, D5S818, D7S820, D13S317, D16S539, HUMCSF1PO, and S159 as detected with the Hitachi FMBIO® II Fluorescent Scanner In this example, two DNA templates were each amplified simultaneously at each of three different locus combinations selected from the loci D3S1358, HUMTH01, D21S11, D18S51, G475, Amelogenin, HUMvWFA31, D8S1179, HUMTPOX, HUMFIBRA, D5S818, D7S820, D13S317, D16S539, HUMCSF1PO and S159, Amplification of each locus combination included 5 ng template in a single reaction vessel containing 25 μl of 1× Gold ST*R Buffer (50 mM KCl, 10 mM Tris-HCl (pH 8.3 at 25° C.), 0.1% Triton X-100, 1.5 mM $MgCl_2$, 160 μg/ml BSA and 200 μM each of dATP, dCTP, dGTP and dTTP).

A GeneAmp® PCR System 9600 (Perkin Elmer, Foster City, Calif.) was employed with the following amplification protocol: 96° C. for 12 min., then 10 cycles of 94° C. for 30 sec., ramp for 68 sec. to 58° C., hold for 30 sec., ramp 50 sec. to 70° C., hold for 45 sec., followed by 22 cycles of 90° C. for 30 sec., ramp 60 sec. to 58° C., hold for 30 sec., ramp for 50 sec, to 70° C., hold for 45 sec., followed by 1 cycle of 60° C. for 30 min.

Thirty-two amplification primers were used in the following concentrations, including 0.225 μM each D3S1358 primers 1 [SEQ ID NO:68] and 2 [FL-SEQ ID NO:69], 0.2 μM each HUMTH01 primers 1 [FL-SEQ ID NO:66] and 2 [SEQ ID NO:67], 1.0 μM each D21S11 primers 1 [SEQ ID NO:64] and 2 [FL-SEQ ID NO:65], 1.0 μM each D18S51 primers 1 [FL-SEQ ID NO:62] and 2 [SEQ ID NO:63], 2.8 μM each G475 primers 1 [FL-SEQ ID NO:88] and 2 [SEQ ID NO:89], 0.2 μM each Amelogenin primers 1 [TMR-SEQ ID NO:86] and 2 [SEQ ID NO:87], 0.3 μM each HUMvWFA31 primers 1 [SEQ ID NO:76] and 2 [TMR-SEQ ID NO:40], 1.5 μM each D8S1179 primers 1 [SEQ ID NO:74] and 2 [TMR-SEQ ID NO:75], 0.2 μM each HUMTPOX primers 1 [SEQ ID NO:72] and 2 [TMR-SEQ ID NO:73], 2.0 μM each HUMFIBRA primers 1 [TMR-SEQ ID NO:70] and 2 [SEQ ID NO:71], 0.55 μM each D5S818 primers 1 [SEQ ID NO:84] and 2 [FL-SEQ ID NO:85], 1.1/M each D13S317 primers 1 [FL-SEQ ID NO:82] and 2 [FL-SEQ ID NO:83], 1.7 μM each D7S820 primers 1 [FL-SEQ ID NO:80] and 2 [SEQ ID NO:81], 3.3 μM each D16S539 primers 1 [SEQ ID NO:29] and 2 [FL-SEQ ID NO:79], 0.5 μM each HUMCSF1PO primers 1 [SEQ ID NO:77] and 2 [FL-SEQ ID NO:78], 2.0 μM each S159 primers 1 [SEQ ID NO:90] and 2 [FL-SEQ ID NO:91].

In the first locus combination, each template was amplified using 2.5 U of AmpliTaq Gold™ DNA Polymerase and primers for each locus used in the concentrations described above for the loci D3S1358, HUMTH01, D21S11, D18S51, G475, Amelogenin, HUMvWFA31, D8S1179, HUMTPOX, and HUMFIBRA. In the second locus combination, all thirty-two primers, above, at the described concentrations, and 4 U of AmpliTaq Gold™ DNA Polymerase were used to amplify DNA templates at all sixteen loci, D3S1358, HUMTH01, D21S11, D18S51, G475, Amelogenin, HUMvWFA31, D8S1179, HUMTPOX, HUMFIBRA, D5S818, D7S820, D13S317, D16S539, HUMCSF1PO and S159 in a single reaction vessel. In the third combination, each template was amplified using 1.5 U of AmpliTaq Gold™ DNA Polymerase and primers for each locus used in the concentrations described above for the loci D5S818, D7S820, D13S317, D16S539, HUMCSF1PO and S159.

Amplification products were separated by electrophoresis through a 0.4 mm thick 4% denaturing polyacrylamide gel (19:1 ratio of acrylamide to bis-acrylamide) which contained 7 M urea (Sambrook et al., (1989)), and which was chemically cross-linked to 2 glass plates (Kobayashi, Y. (1988), BRL Focus 10: 73–74). DNA samples were mixed with 3.5 μl, of a loading solution (10 mM NaOH, 95% formamide, 0.05% bromophenol blue) and 0.5 μl of an internal lane size standard, denatured at 95° C. for 2 min., and chilled on ice prior to loading. The separated products were visualized by detection of the fluorescent signals using the Hitachi FMBIO® II fluorescent scanner (Hitachi Software Engineering America, Ltd. South San Francisco, Calif.). Band pass filters at 505 nm and 585 nm, respectively, were used for the detection of fluorescein-labeled loci and carboxytetramethylrhodamine-labeled loci, respectively. A band pass filter of 650 nm was used for detection of the internal lane standard (size standard data, not shown).

Figure 4A:
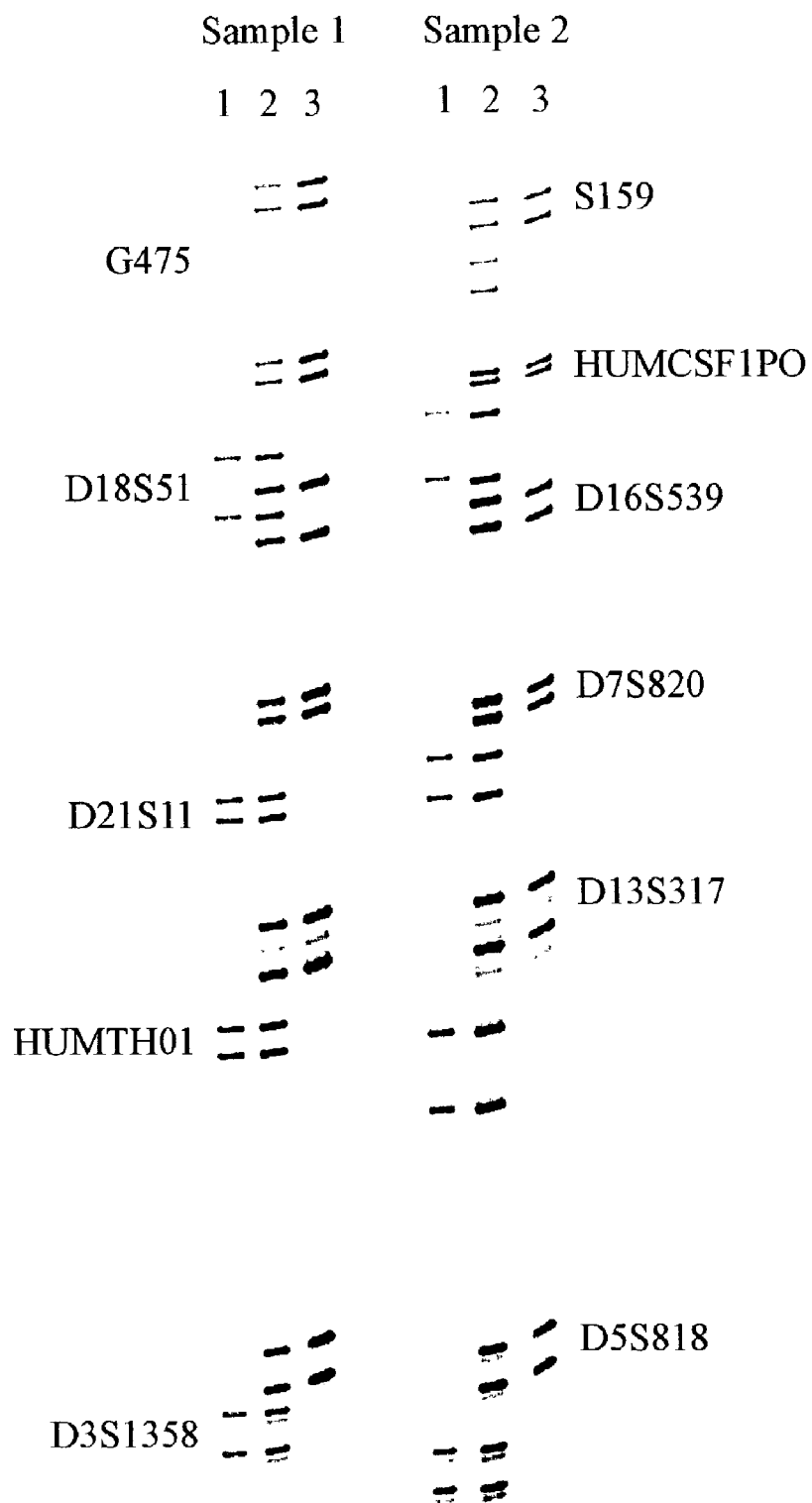

Reference is made to FIGS. 4A and 4B, which display the fragments resulting from each amplification reaction. FIG. 4A shows the results from the 505 nm scan (Fluorescein channel) and FIG. 4B shows the results from the 585 nm scan (carboxy-tetramethylrhodamine channel) of the same lanes of the polyacrylamide gel. For each DNA template, lane 1 shows the results of the DNA sample which has been simultaneously co-amplified for the loci D3S1358, HUMTH01, D21S11, D18S51, G475, Amelogenin, HUMvWFA31, D8S1179, HUMTPOX, and HUMFIBRA. Lane 2 shows the results of the DNA sample simultaneously co-amplified for the loci D3S1358, HUMTH01, D21S11, D18S51, G475, Amelogenin, HUMvWFA31, D8S1179, HUMTPOX, HUMFIBRA, D5S818, D13S317, D7S820, D16S539, HUMCSF1PO, and S159. Lane 3 shows the results of the DNA sample simultaneously co-amplified for the loci D5S818, D13S317, D7S820, D16S539, HUMCSF1PO, and S159.

Example 5

Fluorescent Detection of Multiplex Amplification of Loci D3S1358, HUMTH01, D21S11, D18S51, G475, Amelogenin, HUMvWFA31, D8S1179, HUMTPOX, HUMFIBRA, D5S818, D7S820, D13S317, D16S539, HUMCSF1PO, and S159 as detected with the Hitachi FMBIO® II Fluorescent Scanner In this example, two DNA templates were each amplified simultaneously at each of two different locus combinations selected from the loci D3S1358, HUMTH01, D21S11, D18S51, G475, Amelogenin, HUMvWFA31, D8S1179, HUMTPOX, HUMFIBRA, D5S818, D7S820, D13S317, D16S539, HUMCSF1PO and S159. Amplification of each locus combination included 5 ng template in a single reaction vessel containing 25 μl of 1× Gold ST*R Buffer (50 mM KCl, 10 mM Tris-HCl (pH 8.3 at 25° C.), 0.1% Triton X-100, 1.5 mM $MgCl_2$, 160 μg/ml BSA and 200 μM each of dATP, dCTP, dGTP and dTTP).

A GeneAmp® PCR System 9600 (Perkin Elmer, Foster City, Calif.) was employed with the following amplification protocol: 96° C. for 12 min., then 10 cycles of 94° C. for 30 sec., ramp for 68 sec. to 58° C., hold for 30 sec., ramp 50 sec. to 70° C., hold for 45 sec., followed by 22 cycles of 90° C. for 30 sec., ramp 60 sec. to 58° C., hold for 30 sec., ramp for 50 sec, to 70° C., hold for 45 sec., followed by 1 cycle of 60° C. for 30 min.

Thirty-two amplification primers were used in the following concentrations, including 0.225 μM each D3S1358 primers 1 [SEQ ID NO:68] and 2 [FL-SEQ ID NO:69], 0.2 μM each HUMTH01 primers 1 [FL-SEQ ID NO:66] and 2 [SEQ ID NO:67], 1.0 μM each D21S111 primers 1 [SEQ ID NO:64] and 2 [FL-SEQ ID NO:65], 1.0 μM each D18S51 primers 1 [FL-SEQ ID NO:62] and 2 [SEQ ID NO:63], 2.8 μM each G475 primers 1 [SEQ ID NO:88] and 2 [FL-SEQ ID NO:94], 0.2 μM each Amelogenin primers 1 [TMR-SEQ ID NO:86] and 2 [SEQ ID NO:87], 0.3 μM each HUMvWFA31 primers 1 [SEQ ID NO:76] and 2 [TMR-SEQ ID NO:40], 1.5 μM each D8S1179 primers 1 [SEQ ID NO:74] and 2 [TMR-SEQ ID NO:75], 0.2 μM each HUMTPOX primers 1 [SEQ ID NO:72] and 2 [TMR-SEQ ID NO:73], 2.0 μM each HUMFIBRA primers 1 [TMR-SEQ ID NO:70] and 2 [SEQ ID NO:71], 0.55 μM each D5S818 primers 1 [SEQ ID NO:84] and 2 [FL-SEQ ID NO:85], 1.1 μM each D13S317 primers 1 [SEQ ID NO:82] and 2 [FL-SEQ ID NO:83], 1.7 μM each D7S820 primers 1 [FL-SEQ ID NO:80] and 2 [SEQ ID NO:81], 3.3 μM each D16S539 primers 1 [SEQ ID NO:29] and 2 [FL-SEQ ID NO:79], 0.5 μM each HUMCSF1PO primers 1 [SEQ ID NO:77] and 2 [FL-SEQ ID NO:78], 2.0 μM each S159 primers 1 [SEQ ID NO:95] and 2 [FL-SEQ ID NO:96].

In the first locus combination, each template was amplified using 2.5 U of AmpliTaq Gold™ DNA Polymerase and primers for each locus used in the concentrations described above for the loci D3S1358, HUMTH01, D21S11, D18S51, G475, Amelogenin, HUMvWFA31, D8S1179, HUMTPOX, and HUMFIBRA. In the second locus combination, all thirty-two primers, above, at the described concentrations, and 4 U of AmpliTaq Gold™ DNA Polymerase were used to amplify DNA templates at all sixteen loci, D3S1358, HUMTH01, D21 S11, D18S51, G475, Amelogenin, HUMvWFA31, D8S1179, HUMTPOX, HUMFIBRA, D5S818, D7S820, D13S317, D16S539, HUMCSF1PO and S159 in a single reaction vessel.

The separation and visualization of amplified products were as described in Example 4.

Figure 5A:
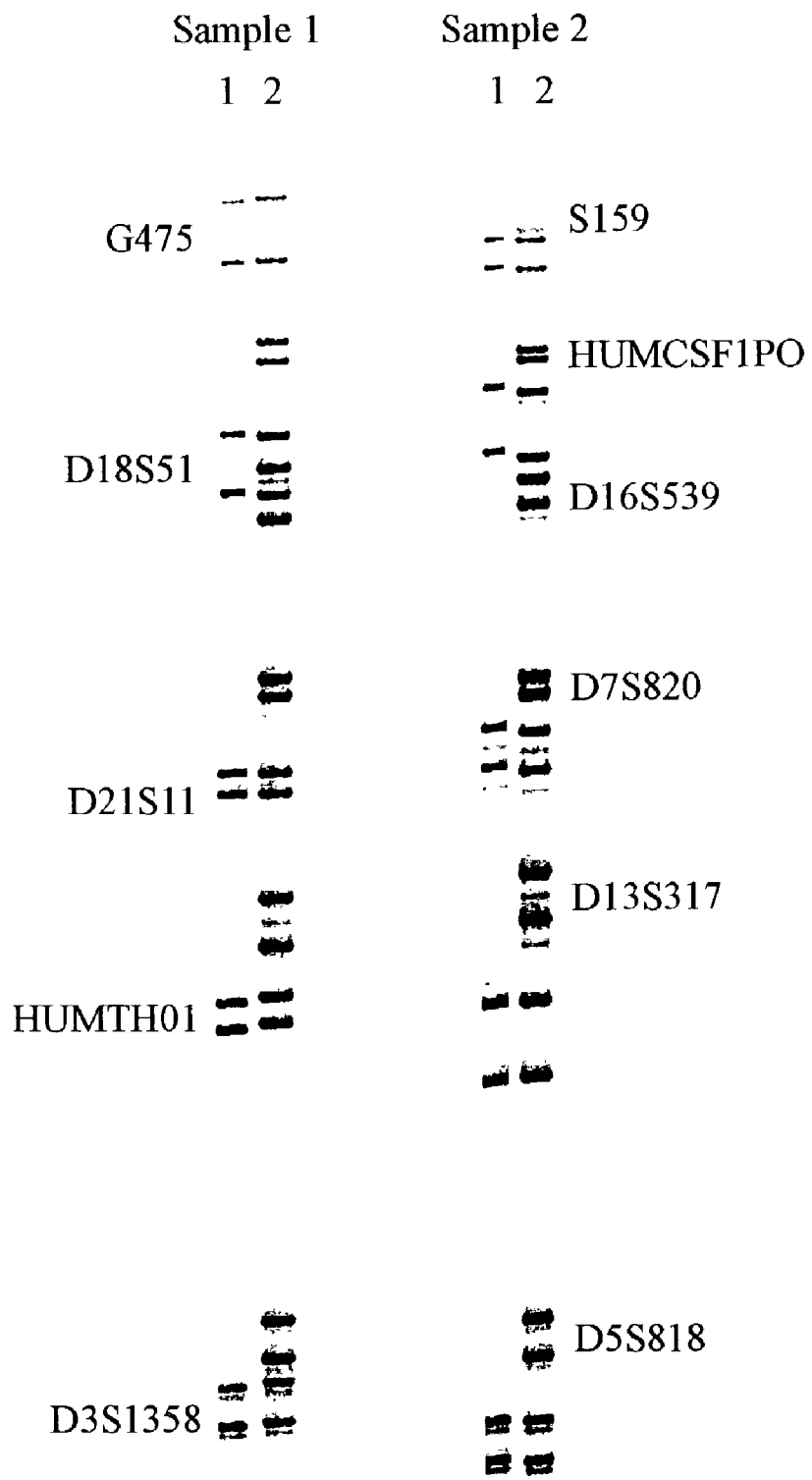

Reference is made to FIGS. 5A and 5B, which display the fragments resulting from each amplification reaction. FIG. 5A shows the results from the 505 nm scan (Fluorescein channel) and FIG. 5B shows the results from the 585 nm scan (carboxy-tetramethylrhodamine channel) of the same lanes of the polyacrylamide gel. For each template, lane 1 shows the results of the DNA sample simultaneously co-amplified for the loci D3S1358, HUMTH01, D21S11, D18S51, G475, Amelogenin, HUMvWFA31, D8S1179, HUMTPOX, and HUMFIBRA and lane 2 shows the results of the DNA sample simultaneously co-amplified for the loci D3S1358, HUMTH01, D21S11, D18S51, G475, Amelogenin, HUMvWFA31, D8S1179, HUMTPOX, HUMFIBRA, D5S818, D13S317, D7S820, D16S539, HUMCSF1PO, and S159.

Example 6

Fluorescent Detection of Multiplex Amplification of Loci D3S1358, HUMTH01, D21S11, D18S51, S159, Amelogenin, HUMvWFA31, D8S1179, HUMTPOX, HUMFIBRA, D5S818, D7S820, D13S317, D16S539, HUMCSF1PO, and C221 as detected with the Hitachi FMBIO® II Fluorescent Scanner In this example, two DNA templates were each amplified simultaneously at each of three different locus combinations selected from the loci D3S1358, HUMTH01, D21S11, D18S51, S159, Amelogenin, HUMvWFA31, D8S1179, HUMTPOX, HUMFIBRA, D5S818, D7S820, D13S317, D16S539, HUMCSF1PO and C221. Amplification of each locus combination included 10 ng template in a single reaction vessel containing 25 µl of 1× Gold ST*R Buffer (50 mM KCl, 10 mM Tris-HCl (pH 8.3 at 25° C.), 0.1% Triton X-100, 1.5 mM MgCl$_2$, 160 µg/ml BSA and 200 µM each of dATP, dCTP, dGTP and dTTP).

A GeneAmp® PCR System 9600 (Perkin Elmer, Foster City, Calif.) was employed with the following amplification protocol: 96° C. for 12 min., then 10 cycles of 94° C. for 30 sec., ramp for 68 sec. to 60° C., hold for 30 sec., ramp 50 sec. to 70° C., hold for 45 sec., followed by 20 cycles of 90° C. for 30 sec., ramp 60 sec. to 60° C., hold for 30 sec., ramp for 50 sec, to 70° C., hold for 45 sec., followed by 1 cycle of 60° C. for 30 min.

Thirty-two amplification primers were used in the following concentrations, including 0.75 µM each D3S1358 primers 1 [SEQ ID NO:106] and 2 [FL-SEQ ID NO:69], 0.3 µM each HUMTH01 primers 1 [FL-SEQ ID NO:38] and 2 [SEQ ID NO:103], 2.0 µM each D21S11 primers 1 [SEQ ID NO:64] and 2 [FL-SEQ ID NO:65], 0.3 µM each D18S51 primers 1 [FL-SEQ ID NO:101] and 2 [SEQ ID NO:102], 2.0 µM each S159 primers 1 [SEQ ID NO:92] and 2 [FL-SEQ ID NO:93], 0.15 µM each Amelogenin primers 1 [TMR-SEQ ID NO:105] and 2 [SEQ ID NO:87], 1.0 µM each HUMvWFA31 primers 1 [SEQ ID NO:76] and 2 [TMR-SEQ ID NO:40], 1.25 µM each D8S1179 primers 1 [TMR-SEQ ID NO:104] and 2 [SEQ ID NO:75], 0.75 µM each HUMTPOX primers 1 [TMR-SEQ ID NO:72] and 2 [SEQ ID NO:73], 1.5 µM each HUMFIBRA primers 1 [TMR-SEQ ID NO:70] and 2 [SEQ ID NO:107], 0.55 µM each D5S818 primers 1 [SEQ ID NO:84] and 2 [FL-SEQ ID NO:85], 1.1 µM each D13S317 primers 1 [SEQ ID NO:3] and 2 [FL-SEQ ID NO:4], 1.7 µM each D7S820 primers 1 [FL-SEQ ID NO:80] and 2 [SEQ ID NO:81], 3.3 µM each D16S539 primers 1 [FL-SEQ ID NO:29] and 2 [SEQ ID NO:97], 0.25 µM each HUMCSF1PO primers 1 [SEQ ID NO:77] and 2 [FL-SEQ ID NO:98], 1.0 µM each C221 primers 1 [FL-SEQ ID NO:99] and 2 [SEQ ID NO: 100].

In the first locus combination, each template was amplified using 2.5 U of AmpliTaq Gold™ DNA Polymerase and primers for each locus used in the concentrations described above for the loci D3S1358, HUMTH01, D21 S11, D18S51, S159, Amelogenin, HUMvWFA31, D8S1179, HUMTPOX, and HUMFIBRA. In the second locus combination, all thirty-two primers, above, at the described concentrations and 4 U of AmpliTaq Gold™ DNA Polymerase were used to amplify DNA templates at all sixteen loci, D3S1358, HUMTH01, D21S11, D18S51, S159, Amelogenin, HUMvWFA31, D8S1179, HUMTPOX, HUMFIBRA, D5S818, D7S820, D13S317, D16S539, HUMCSF1PO and C221 in a single reaction vessel. In the third combination, each template was amplified using 1.5 U of AmpliTaq Gold™ DNA Polymerase and primers for each locus used in the concentrations described above for the loci D5S818, D7S820, D13S317, D16S539, HUMCSF1PO and C221.

The amplification products were separated and detected as described in Example 4, except that each sample of amplification products was diluted 1:4 in 1× STR Buffer (50 mM KCl, 10 mM Tris-HCl (pH 8.3 at 25° C.), 0.1% Triton X-100, 1.5 mM MgCl$_2$, and 200 µM each of dATP, dCTP, dGTP and dTTP). The diluted amplification products (2.5 µ) were mixed with 2.5 µl of a loading solution (10 mM NaOH, 95% formamide, 0.05% bromophenol blue), without an internal lane standard, denatured at 95° C. for 2 min., and chilled on ice prior to loading.

Figure 6A:
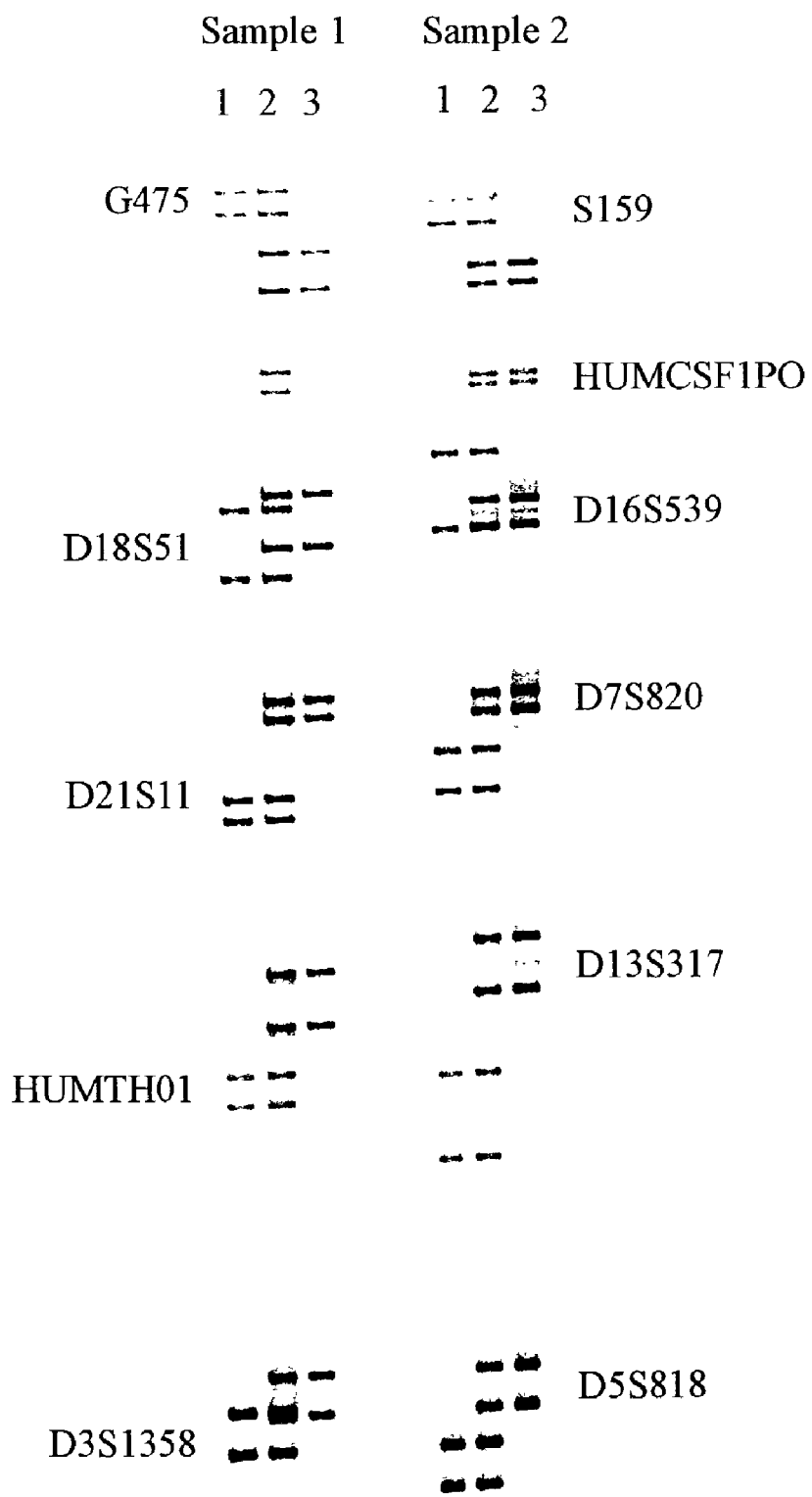
FIGS. 6A and 6B are laser printed images of the results of fluorescent detection of the products of simultaneous amplification of the loci D3S1358, D5S818, D7S820, D8S1179, D13S317, D16S539, D18S51, D21S11, HUMCSF1PO, HUMFIBRA, HUMTH01, HUMTPOX, HUMvWFA31, C221, S159, and Amelogenin as detected using the fluorescein channel (FIG. 6A) and carboxy-tetramethylrhodamine channel (FIG. 6B) of a Hitachi FMBIO® II Fluorescent Scanner, as described in Example 6.
Figure 6B:
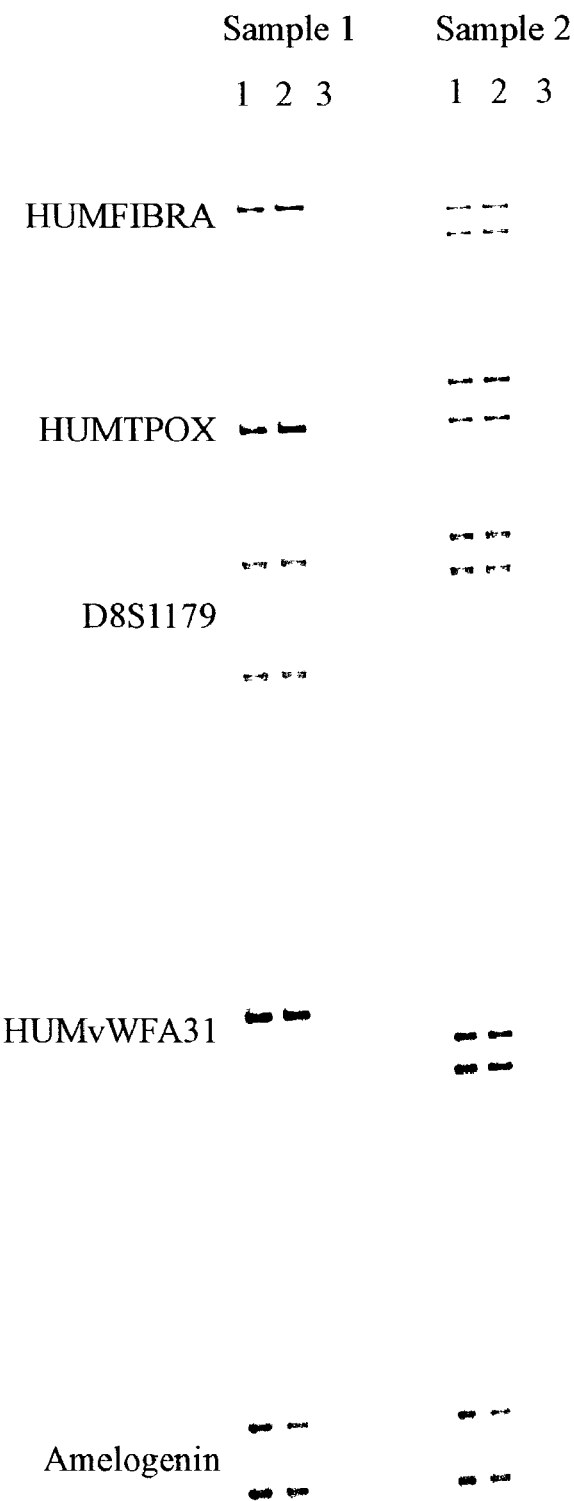

Reference is made to FIGS. 6A and 6B, which display the fragments resulting each amplification reaction. FIG. 6A shows the results from the 505 nm scan (Fluorescein channel) and FIG. 6B shows the results from the 585 nm scan (carboxy-tetramethylrhodamine channel) of the same lanes of the polyacrylamide gel. For each DNA template, lane 1 shows the results of the DNA sample simultaneously co-amplified for the loci D3S1358, HUMTH01, D21S11, D18S51, S159, Amelogenin, HUMvWFA31, D8S1179, HUMTPOX, and HUMFIBRA. Lane 2 shows the results of the DNA sample simultaneously co-amplified for the loci D3S1358, HUMTH01, D21 S11, D18S51, G475, Amelogenin, HUMvWFA31, D8S1179, HUMTPOX, HUMFIBRA, D5S818, D13S317, D7S820, D16S539, HUMCSF1PO, and C221. Lane 3 shows the results of the DNA sample simultaneously co-amplified for the loci D5S818, D13S317, D7S820, D16S539, HUMCSF1PO, and C221.

What is claimed is:

1. A kit for simultaneously analyzing a set of loci of genomic DNA, comprising oligonucleotide primers for co-amplifying a set of loci of the genomic DNA to be analyzed, wherein the primers are in one or more containers, wherein the primers are designed to co-amplify a set of at least sixteen loci which can be co-amplified, comprising D3S1358, HUMTH01, D21S11, D18S51, G475, Amelogenin, HUMvWFA31, D8S1179, HUMTPOX, HUMFIBRA, D5S818, D7S820, D13S317, D16S539, HUMCSF1PO, and S159.

2. A kit for simultaneously analyzing a set of loci of genomic DNA, comprising oligonucleotide primers for co-amplifying a set of loci of the genomic DNA to be analyzed, wherein the primers are in one or more containers, wherein the primers are designed to co-amplify a set of at least sixteen loci which can be co-amplified, comprising D3S1358, HUMTH01, D21S11, D18S51, S159, Amelogenin, HUMvWFA31, D8S1179, HUMTPOX, HUMFIBRA, D5S818, D7S820, D13S317, D16S539, HUMCSF1PO, and C221.

3. The kit of claim 1, wherein at least one oligonucleotide primer has a sequence selected from one of the groups of primer sequences consisting of:

SEQ ID NO:68, SEQ ID NO:69, and SEQ ID NO:106, for the locus D3S1358;

SEQ ID NO:37, SEQ ID NO:38, SEQ ID NO:66, SEQ ID NO:67, and SEQ ID NO:103, for the locus HUMTH01;

SEQ ID NO:64 and SEQ ID NO:65, for the locus D21S11;

SEQ ID NO:62, SEQ ID NO:63, SEQ ID NO:101, and SEQ ID NO:102, for the locus D18S51;

SEQ ID NO:88, SEQ ID NO:89, and SEQ ID NO:94, for the locus G475;

SEQ ID NO:86, SEQ ID NO:87, and SEQ ID NO:105, for the Amelogenin locus;

SEQ ID NO:39, SEQ ID NO:40, SEQ ID NO:59, SEQ ID NO:60, and SEQ ID NO:76, for the locus HUMvWFA31;

SEQ ID NO:74, SEQ ID NO:75, and SEQ ID NO:104, for the locus D8S1179;

SEQ ID NO:35, SEQ ID NO:36, SEQ ID NO:72, and SEQ ID NO:73, for the locus HUMTPOX;

SEQ ID NO:70, SEQ ID NO:71, and SEQ ID NO:107, for the locus HUMFIBRA;

SEQ ID NO:5, SEQ ID NO:6, SEQ ID NO:84, and SEQ ID NO:85, for the locus D5S818;

SEQ ID NO:1, SEQ ID NO:2, SEQ ID NO:80, and SEQ ID NO:81, for the locus D7S820;

SEQ ID NO:3, SEQ ID NO:4, SEQ ID NO:82, and SEQ ID NO:83, for the locus D13S317;

SEQ ID NO:29, SEQ ID NO:30, SEQ ID NO:58, SEQ ID NO:79, and SEQ ID NO:97, for the locus D16S539;

SEQ ID NO:33, SEQ ID NO:34, SEQ ID NO:77, SEQ ID NO:78, and SEQ ID NO:98, for the locus HUMCSF1PO; and SEQ ID NO:90, SEQ ID NO:91, SEQ ID NO:92, SEQ ID NO:93, SEQ ID NO:95, and SEQ ID NO:96, for the locus S159.

4. The kit of claim 2, wherein at least one oligonucleotide primer has a sequence selected from one of the groups of primer sequences consisting of:

SEQ ID NO:68, SEQ ID NO:69, and SEQ ID NO:106, for the locus D3S1358;

SEQ ID NO:37, SEQ ID NO:38, SEQ ID NO:66, SEQ ID NO:67, and SEQ ID NO:103, for the locus HUMTH01;

SEQ ID NO:64 and SEQ ID NO:65, for the locus D21S11;

SEQ ID NO:62, SEQ ID NO:63, SEQ ID NO:101, and SEQ ID NO:102, for the locus D18S51;

SEQ ID NO:88, SEQ ID NO:89, and SEQ ID NO:94, for the locus S159;

SEQ ID NO:86, SEQ ID NO:87, and SEQ ID NO:105, for the Amelogenin locus;

SEQ ID NO:39, SEQ ID NO:40, SEQ ID NO:59, SEQ ID NO:60, and SEQ ID NO:76, for the locus HUMvWFA31;

SEQ ID NO:74, SEQ ID NO:75, and SEQ ID NO:104, for the locus D8S1179;

SEQ ID NO:35, SEQ ID NO:36, SEQ ID NO:72, and SEQ ID NO:73, for the locus HUMTPOX;

SEQ ID NO:70, SEQ ID NO:71, and SEQ ID NO:107, for the locus HUMFIBRA;

SEQ ID NO:5, SEQ ID NO:6, SEQ ID NO:84, and SEQ ID NO:85, for the locus D5S818;

SEQ ID NO:1, SEQ ID NO:2, SEQ ID NO:80, and SEQ ID NO:81, for the locus D7S820;

SEQ ID NO:3, SEQ ID NO:4, SEQ ID NO:82, and SEQ ID NO:83, for the locus D13S317;

SEQ ID NO:29, SEQ ID NO:30, SEQ ID NO:58, SEQ ID NO:79, and SEQ ID NO:97, for the locus D16S539;

SEQ ID NO:33, SEQ ID NO:34, SEQ ID NO:77, SEQ ID NO:78, and SEQ ID NO:98, for the locus HUMCSF1PO; and SEQ ID NO:99 and SEQ ID NO:100, for the locus C221.

5. A kit for simultaneously analyzing a set of loci of genomic DNA, comprising oligonucleotide primers for co-amplifying a set of loci of the genomic DNA to be analyzed, wherein the primers are in one or more containers, wherein the primers are designed to co-amplify a set of loci from one or more DNA samples, comprising short tandem repeat loci D3S1358, D5S818, D7S820, D8S1179, D13S317, D16S539, D18S51, D21S11, HUMCSF1PO, HUMFIBRA, HUMTH01, HUMTPOX, HUMvWFA31, and a locus selected from the group consisting of G475, S159, C221, and Amelogenin.

6. The kit of claim 5, wherein at least one oligonucleotide primer has a sequence selected from one of the groups of primer sequences consisting of:

SEQ ID NO:62, SEQ ID NO:63, SEQ ID NO:101, and SEQ ID NO:102, when one of the loci in the set is D18S51;

SEQ ID NO:64 and SEQ ID NO:65, for the locus D21S11;

SEQ ID NO:37, SEQ ID NO:38, SEQ ID NO:66, SEQ ID NO:67, and SEQ ID NO:103, for the locus HUMTH01;

SEQ ID NO:68, SEQ ID NO:69, and SEQ ID NO:106, for the locus D3S1358;

SEQ ID NO:70, SEQ ID NO:71, and SEQ ID NO:107, for the locus HUMFIBRA;

SEQ ID NO:35, SEQ ID NO:36, SEQ ID NO:72, and SEQ ID NO:73, for the locus HUMTPOX;

SEQ ID NO:74, SEQ ID NO:75, and SEQ ID NO:104, for the locus D8S1179;

SEQ ID NO:39, SEQ ID NO:40, SEQ ID NO:59, SEQ ID NO:60, and SEQ ID NO:76, for the locus HUMvWFA31;

SEQ ID NO:33, SEQ ID NO:34, SEQ ID NO:77, SEQ ID NO:78, and SEQ ID NO:98, for the locus HUMCSF1PO;

SEQ ID NO:29, SEQ ID NO:30, SEQ ID NO:58, SEQ ID NO:79, and SEQ ID NO:97, for the locus D16S539;

SEQ ID NO:1, SEQ ID NO:2, SEQ ID NO:80, and SEQ ID NO:81, for the locus D7S820;

SEQ ID NO:3, SEQ ID NO:4, SEQ ID NO:82, and SEQ ID NO:83, for the locus D13S317;

SEQ ID NO:5, SEQ ID NO:6, SEQ ID NO:84, and SEQ ID NO:85, for the locus D5S818;

SEQ ID NO:88, SEQ ID NO:89, and SEQ ID NO:94, for the locus G475;

SEQ ID NO:90, SEQ ID NO:91, SEQ ID NO:92, SEQ ID NO:93, SEQ ID NO:95, and SEQ ID NO:96, for the locus S159;

SEQ ID NO:99 and SEQ ID NO:100, for the locus C221; and

SEQ ID NO:86, SEQ ID NO:87, and SEQ ID NO:105, for the Amelogenin locus.

\* \* \* \* \*

UNITED STATES PATENT AND TRADEMARK OFFICE
CERTIFICATE OF CORRECTION

| | |
|---|---|
| PATENT NO. | : 7,008,771 B1 |
| APPLICATION NO. | : 10/236577 |
| DATED | : March 7, 2006 |
| INVENTOR(S) | : James W. Schumm et al. |

It is certified that error appears in the above-identified patent and that said Letters Patent is hereby corrected as shown below:

On The Title Page, Item -56-
    In (56) References Cited, U.S. PATENT DOCUMENTS, after U.S. patent "5,843,660 A, 12/1998, Schumm et al.," insert --6,013,444 A, 1/2000, Dau et al.--.

On The Title Page, Item -56-
    In (56) References Cited, FOREIGN PATENT DOCUMENTS, after foreign patent "DE 38 34 636 C2, 4/1990," insert --EP 0 846 775, 6/1998--.

On The Title Page, Item -56-
    In (56) References Cited, FOREIGN PATENT DOCUMENTS, after foreign patent "WO 96/10648, 4/1996," insert --WO 97/39138, 10/1997--.

On The Title Page, Item -56-
    In (56) References Cited, OTHER PUBLICATIONS, after reference "Niezgoda, Stephen J. Jr., et al., "The FBI Laboratory's Combined DNA Index System Program," (1995) The Sixth International Symposium on Human Identification, pp. 149-153," insert the following references:

--Amiott, et al. "Incorporating high quality markers into forensically useful mulitplexes," Human Identification Symposium Proceedings: 9th International Symposium on Human Identification, October 8-10, 1998, pp. 2-6.

Lins, A. et al., "Development and population study of an eight-locus short tandem repeat (STR) multiplex system," J. of Forensic Sciences, (Nov. 1998) 43(6) 1168-80.

Lin, Z. et al., "Multiplex genotype determination at a large number of gene loci," Proceedings of the National Academy of Sciences of the United States of America, (March 19, 1996) 93(6) pp. 2582-7.

McKeown B., et al. "Increasing the size of PCR products without redesigning primer building sequences," Nucleic Acids Research, (June 25, 1995) pp. 2337-8.

Oldroyd et al., "A highly discriminating octoplex short tandem repeat polymerase chain reaction suitable for human individual identification," Electrophoresis Vol. 16, pp. 334-337.

Schumm et al., "Pentanucleotide repeats: Highly polymorphic genetic markers displaying minimal stutter artifact," Human Identification Symposium Proceedings: 9th International Symposium on Human Identification, October 8-10, 1998, pp. 24-37.

UNITED STATES PATENT AND TRADEMARK OFFICE
CERTIFICATE OF CORRECTION

| | |
|---|---|
| PATENT NO. | : 7,008,771 B1 |
| APPLICATION NO. | : 10/236577 |
| DATED | : March 7, 2006 |
| INVENTOR(S) | : James W. Schumm et al. |

It is certified that error appears in the above-identified patent and that said Letters Patent is hereby corrected as shown below:

Sparkes, R. et al. "The validation of a 7-locus multiplex STR test for use in forensic casework (II), Artifacts, casework studies and success rates," International J. Legal Medicine (1996) 109(4) pp. 195-204.

"The 9th international symposium on human identification October 8-10, 1998," Profiles in DNA, (Jan. 1999) Vol. 2 No. 3, p. 13 and Table of Contents.--

In (56) References Cited, OTHER PUBLICATIONS:

Page 2, after the Bever, Robert A. et al. reference, "Budowie" should read --Budowle--.

Page 3, under the Hudson, Thomas et al. reference, "Chromsmal" should read --Chromosomal--.

Page 3, under the Kimpton, C. et al. reference, "progiling" should read --profiling--.

Page 3, under the Lohmann, D. et al. reference, "retinolastoma" should read --retinoblastoma--.

Page 3, under the Pftizinger, Helene et al. reference, "Systemns" should read --Systems--.

Page 3, under the Richard, Malanie et al. reference, delete second occurrence of "Repeat (STR)"; "THO01" should read --TH01--; "Flyorescence" should read --Fluorescence--; "Fight" should read --Fifth--

Page 3, under the second Schumm, James W. et al. reference, "help" should read --held--.

Page 3, under the Shuber, Anthony reference, "PCPs" should read --PCRs--.

Page 4, line 1, insert --Symposium-- between 'International' and 'on'

Page 4, under the Williamson, R. et al. reference, "Cenet" should read --Genet--.

Page 4, under the McCabe, E.R. reference, "Sports" should read --Spots--.

UNITED STATES PATENT AND TRADEMARK OFFICE
CERTIFICATE OF CORRECTION

PATENT NO. : 7,008,771 B1
APPLICATION NO. : 10/236577
DATED : March 7, 2006
INVENTOR(S) : James W. Schumm et al.

It is certified that error appears in the above-identified patent and that said Letters Patent is hereby corrected as shown below:

Page 4, under the second Perkin-Elmer Corporation reference, "(1997)" should read --(1998)--; the first "pp." should be deleted.

Page 4, line 1, "Interneational" should read --International--.

Page 4, under the Niezgoda, S.J. reference, "(1997)" should read --(1998)--.

Page 4, after the Werrett, D.J. et al. reference, "Budowie" should read --Budowle--.

Page 5, under the Puers, C. et al. reference, "HUMTH01[AATG]," should read --HUMTH01[AATG]$_n$--.

Page 5, under the Chen, H. et al. reference, "(ATTTT)," should read --(ATTTT)$_n$--.

Page 5, line 2, "Glucocirticoid" should read --Glucocorticoid--.

Page 5, under the Litt, M. et al. reference, "Virto" should read --Vitro--.

Column 1, line 37, delete "a" between 'at' and 'crime'.

Column 5, lines 14 and 15, delete "In another emobidment of the invention, the set of loci selected in step (b) of".

Column 8, line 60, "$(A_2G_xT_yC_z)_n$" should read --$(A_wG_xT_yC_z)_n$--.

Column 15, line 6, "1 3.57" should read --13.57--.

Column 15, line 7, delete "for" between 'conditions' and 'suitable'.

Column 19, line 42, "0.1M" should read --0.1μM--.

Column 20, line 43, "0.3%μM" should read --0.3μM--.

Column 22, line 46, "1.1M" should read --1.1μM--.

UNITED STATES PATENT AND TRADEMARK OFFICE
CERTIFICATE OF CORRECTION

PATENT NO.         : 7,008,771 B1
APPLICATION NO. : 10/236577
DATED              : March 7, 2006
INVENTOR(S)        : James W. Schumm et al.

It is certified that error appears in the above-identified patent and that said Letters Patent is hereby corrected as shown below:

Column 26, line 21, "2.5μ" should read --2.5μl--.

Signed and Sealed this

Eighth Day of April, 2008

JON W. DUDAS
*Director of the United States Patent and Trademark Office*